United States Patent
Moriya et al.

(10) Patent No.: US 10,667,961 B2
(45) Date of Patent: Jun. 2, 2020

(54) ABSORBENT ARTICLE AND WEARABLE ARTICLE INCLUDING ABSORBENT ARTICLE

(71) Applicant: UNICHARM CORPORATION, Shikokuchuo-shi, Ehime (JP)

(72) Inventors: Ayako Moriya, Kanonji (JP); Haruki Toda, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 683 days.

(21) Appl. No.: 15/322,950

(22) PCT Filed: Jun. 11, 2015

(86) PCT No.: PCT/JP2015/066911
§ 371 (c)(1),
(2) Date: Dec. 29, 2016

(87) PCT Pub. No.: WO2016/002471
PCT Pub. Date: Jan. 7, 2016

(65) Prior Publication Data
US 2017/0135869 A1 May 18, 2017

(30) Foreign Application Priority Data
Jun. 30, 2014 (JP) .................. 2014-135461

(51) Int. Cl.
*A61F 13/15* (2006.01)
*A61F 13/20* (2006.01)
(Continued)

(52) U.S. Cl.
CPC ........ *A61F 13/51108* (2013.01); *A61F 13/15* (2013.01); *A61F 13/15731* (2013.01);
(Continued)

(58) Field of Classification Search
CPC ...... A61F 13/15; A61F 13/4704; A61F 13/49; A61F 13/49001; A61F 13/49009;
(Continued)

(56) References Cited

U.S. PATENT DOCUMENTS

2006/0069371 A1* 3/2006 Ohashi ............... A61F 13/4704
604/385.01
2006/0189954 A1* 8/2006 Kudo ................ A61F 13/15203
604/380
(Continued)

FOREIGN PATENT DOCUMENTS

EP 0 768 072 A1 * 4/1997 ............ A61F 13/15
EP 2500003 A1 9/2012
(Continued)

OTHER PUBLICATIONS

International Search Report in PCT/JP2015/066911, dated Aug. 25, 2015.

*Primary Examiner* — Michele M Kidwell
(74) *Attorney, Agent, or Firm* — Hauptman Ham, LLP

(57) ABSTRACT

Provided is an absorbent article in which the shape of projections formed in a predetermined region of a topsheet can be maintained. In this absorbent article: a nonwoven fabric that has a skin-side surface having projections formed thereon is used as a topsheet; and an absorbent body has formed therein a through hole that penetrates the absorbent body in the thickness direction.

14 Claims, 13 Drawing Sheets

(51) Int. Cl.
*A61F 13/511* (2006.01)
*A61F 13/494* (2006.01)
*A61F 13/535* (2006.01)
*A61F 13/47* (2006.01)
*A61F 13/49* (2006.01)
*A61F 13/532* (2006.01)
*A61F 13/70* (2006.01)
*A61F 13/53* (2006.01)
*A61F 13/537* (2006.01)
*A61F 13/505* (2006.01)
*A61F 13/536* (2006.01)
*A61F 13/66* (2006.01)
*A61F 13/534* (2006.01)

(52) U.S. Cl.
CPC ........ *A61F 13/4704* (2013.01); *A61F 13/49* (2013.01); *A61F 13/49001* (2013.01); *A61F 13/494* (2013.01); *A61F 13/49009* (2013.01); *A61F 13/505* (2013.01); *A61F 13/511* (2013.01); *A61F 13/53* (2013.01); *A61F 13/532* (2013.01); *A61F 13/535* (2013.01); *A61F 13/536* (2013.01); *A61F 13/53743* (2013.01); *A61F 13/53747* (2013.01); *A61F 13/66* (2013.01); *A61F 13/70* (2013.01); *A61F 2013/53445* (2013.01)

(58) Field of Classification Search
CPC .... A61F 13/494; A61F 13/505; A61F 13/511; A61F 13/51108; A61F 13/53; A61F 13/535; A61F 13/536; A61F 13/53743; A61F 13/66; A61F 13/70; A61F 2013/53445
See application file for complete search history.

(56) References Cited

U.S. PATENT DOCUMENTS

| | | |
|---|---|---|
| 2007/0298220 A1 | 12/2007 | Noda et al. |
| 2008/0199812 A1* | 8/2008 | Vermeersch ......... B41C 1/1025 430/302 |

FOREIGN PATENT DOCUMENTS

| | | |
|---|---|---|
| JP | 10-502000 A | 2/1998 |
| JP | 2003-204987 A | 7/2003 |
| JP | 2006-95156 A | 4/2006 |
| JP | 2006-230564 A | 9/2006 |
| JP | 2007-37660 A | 2/2007 |
| JP | 2012-125354 A | 7/2012 |
| JP | 2014-18280 A | 2/2014 |
| JP | 2014-73213 A | 4/2014 |
| WO | 96/00545 A1 | 1/1996 |
| WO | 2012/067216 A1 | 5/2012 |
| WO | 2013/005782 A1 | 1/2013 |
| WO | 2014/054649 A1 | 4/2014 |

* cited by examiner

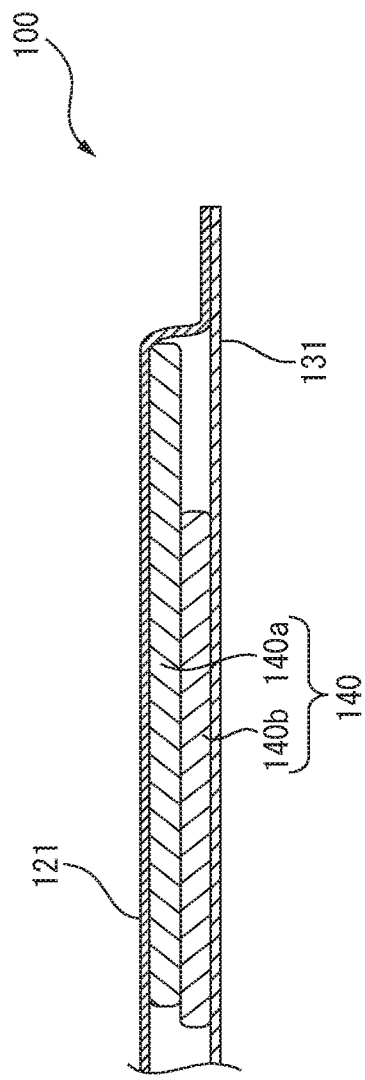
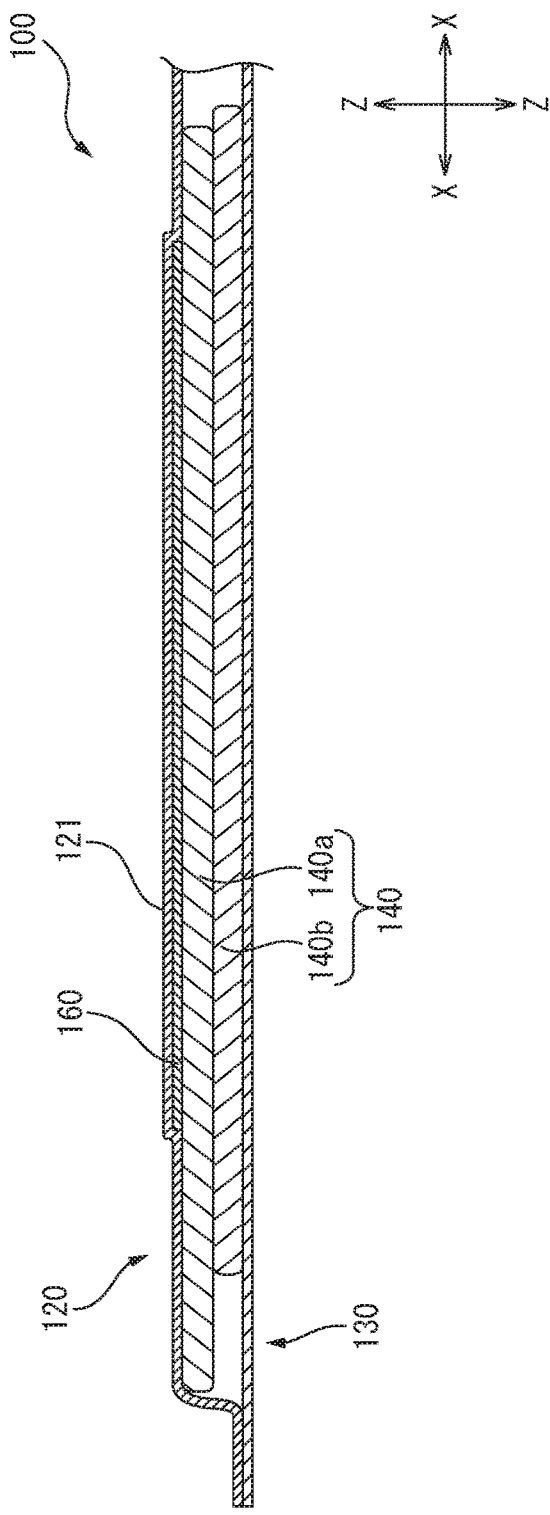

FIG. 6
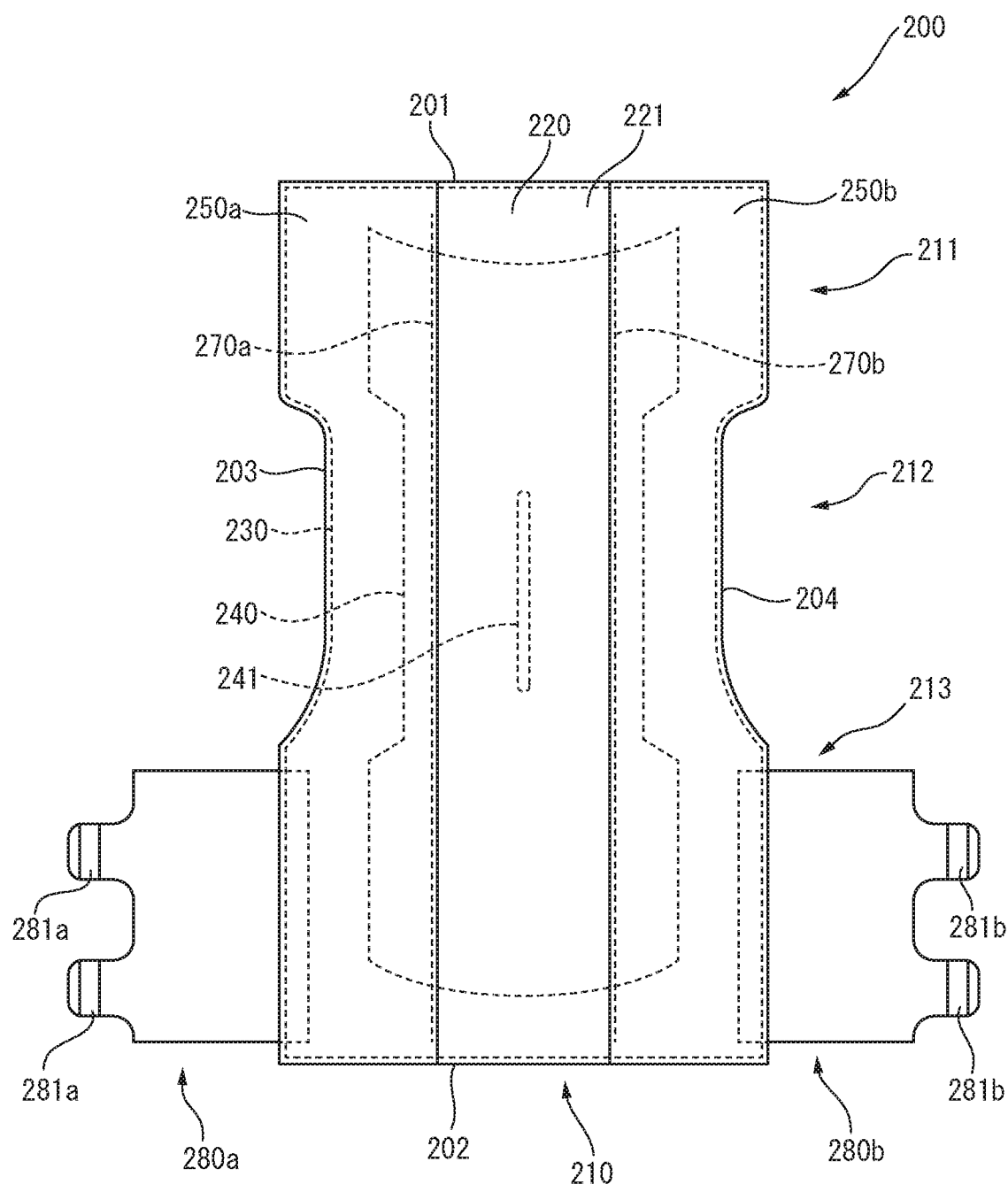
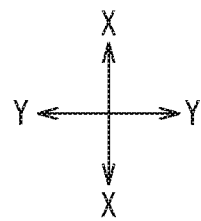

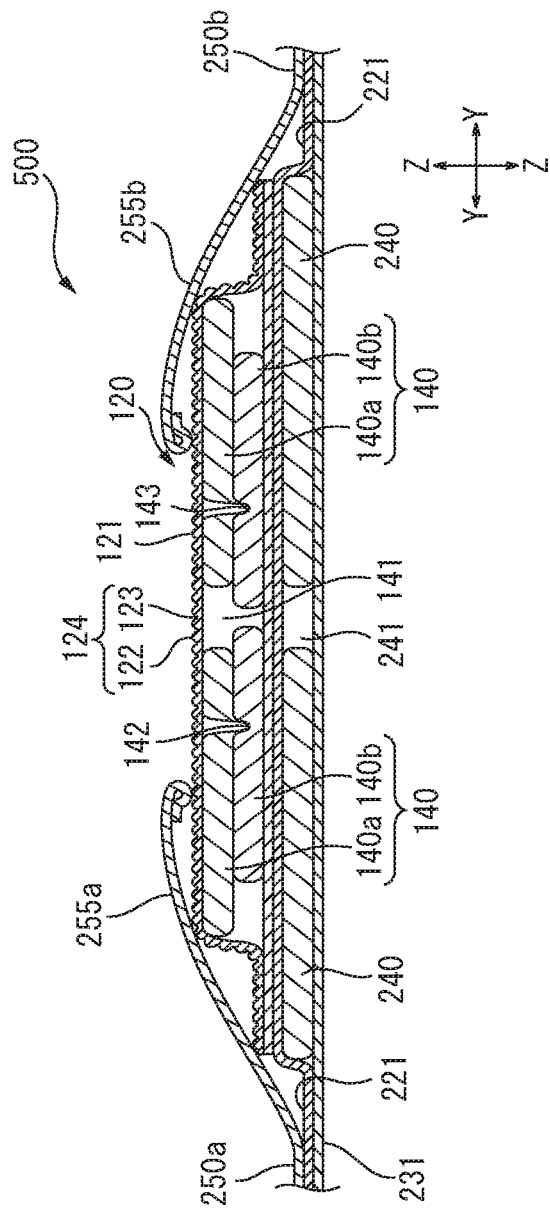

ABSORBENT ARTICLE AND WEARABLE ARTICLE INCLUDING ABSORBENT ARTICLE

RELATED APPLICATIONS

The present application is a National Phase of International Application Number PCT/JP2015/066911, filed Jun. 11, 2015, which claims priority from Japanese Application Number 2014-135461, filed Jun. 30, 2014.

TECHNICAL FIELD

The present invention relates to an absorbent article and to a wearable article provided with an absorbent article.

BACKGROUND ART

Patent Document 1 describes an absorbent article having an absorbent body with rows of perforated holes disposed in the section that is in contact with the genital area of a wearer. With the absorbent article described in Patent Document 1, it is possible to improve the fitting properties of the absorbent article for the wearer's genital area. Moreover, since the section that is in contact with the wearer's genital area does not easily become moist, it is possible to prevent the wearer from feeling discomfort.

Patent Documents 2 to 13 disclose nonwoven fabrics having protrusions formed on a surface, and the use of the nonwoven fabrics as top sheets for absorbent articles. In the nonwoven fabrics described in Patent Documents 2 to 13, it is possible to improve the liquid permeability and touch feeling of the nonwoven fabrics by the protrusions formed on the surface.

CITATION LIST

Patent Documents

Patent Document 1: Japanese Unexamined Patent Publication No. 2006-95156
Patent Document 2: Japanese Unexamined Patent Publication No. 2009-30218
Patent Document 3: Japanese Unexamined Patent Publication No. 2008-23326
Patent Document 4: Japanese Unexamined Patent Publication No. 2008-25079
Patent Document 5: Japanese Unexamined Patent Publication No. 2004-174234
Patent Document 6: Japanese Unexamined Patent Publication No. 2009-160035
Patent Document 7: Japanese Unexamined Patent Publication No. 2009-201964
Patent Document 8: Japanese Unexamined Patent Publication No. 2012-5701
Patent Document 9: Japanese Unexamined Patent Publication No. 2002-187228
Patent Document 10: Japanese Unexamined Patent Publication No. 2003-247155
Patent Document 11: Japanese Unexamined Patent Publication No. 2007-177340
Patent Document 12: Japanese Unexamined Patent Publication No. 2005-350836
Patent Document 13: Japanese Unexamined Patent Publication No. 2010-168715

SUMMARY OF INVENTION

Problems to be Solved by the Invention

When an absorbent article is equipped with a liquid-permeable top sheet having protrusions thereon, the protrusions formed on the top sheet may be collapsed due to the pressure applied to the absorbent article, thereby impairing the functions of the protrusions (for example, an improvement in liquid permeability, an improvement in touch feeling, etc.).

Accordingly, an object of the present invention is to provide an absorbent article comprising a top sheet having protrusions formed thereon, and capable of maintaining the shape of the protrusions formed at a predetermined region (for example, a section which is in contact with the wearer's genital area) of the top sheet, and a wearable article comprising the absorbent article.

Solution to Problem

In order to solve the problems described above, the present invention provides an absorbent article comprising a liquid-permeable top sheet, a liquid-impermeable back sheet, and a liquid-absorbing absorbent body disposed between the top sheet and the back sheet, and having a lengthwise direction, a widthwise direction, and a thickness direction that are mutually orthogonal; wherein the top sheet is a nonwoven fabric with a skin side surface on which protrusions are formed; and wherein the absorbent body has a through-hole penetrating through the absorbent body in the thickness direction or a recess that opens to a side of the top sheet.

The present invention further provides a wearable article comprising an exterior body comprising a liquid-permeable top sheet with a mounting surface on which an absorbent article is to be mounted, and a liquid-impermeable back sheet, and having an abdomen side section, a crotch section and a back side section; and the absorbent article of the present invention mounted on the mounting surface in a detachable manner.

Effects of the Invention

According to the present invention, an absorbent article comprising a top sheet having protrusions formed thereon, and capable of maintaining the shape of the protrusions formed at a predetermined region (for example, a section which is in contact with the wearer's genital area) of the top sheet, and a wearable article comprising the absorbent article is provided.

BRIEF DESCRIPTION OF DRAWINGS

FIG. 4(A) is an end view along line B-B of FIG. 1 (a portion on the abdomen section side),
and FIG. 4(B) is an end view along line B-B of FIG. 1 (a portion on the back section side).
FIG. 6 is a plan view of an exterior body according to an embodiment of the invention.

FIG. 11 is a cross-sectional view along line A-A of FIG. 10.

DESCRIPTION OF EMBODIMENTS

Figure 1:
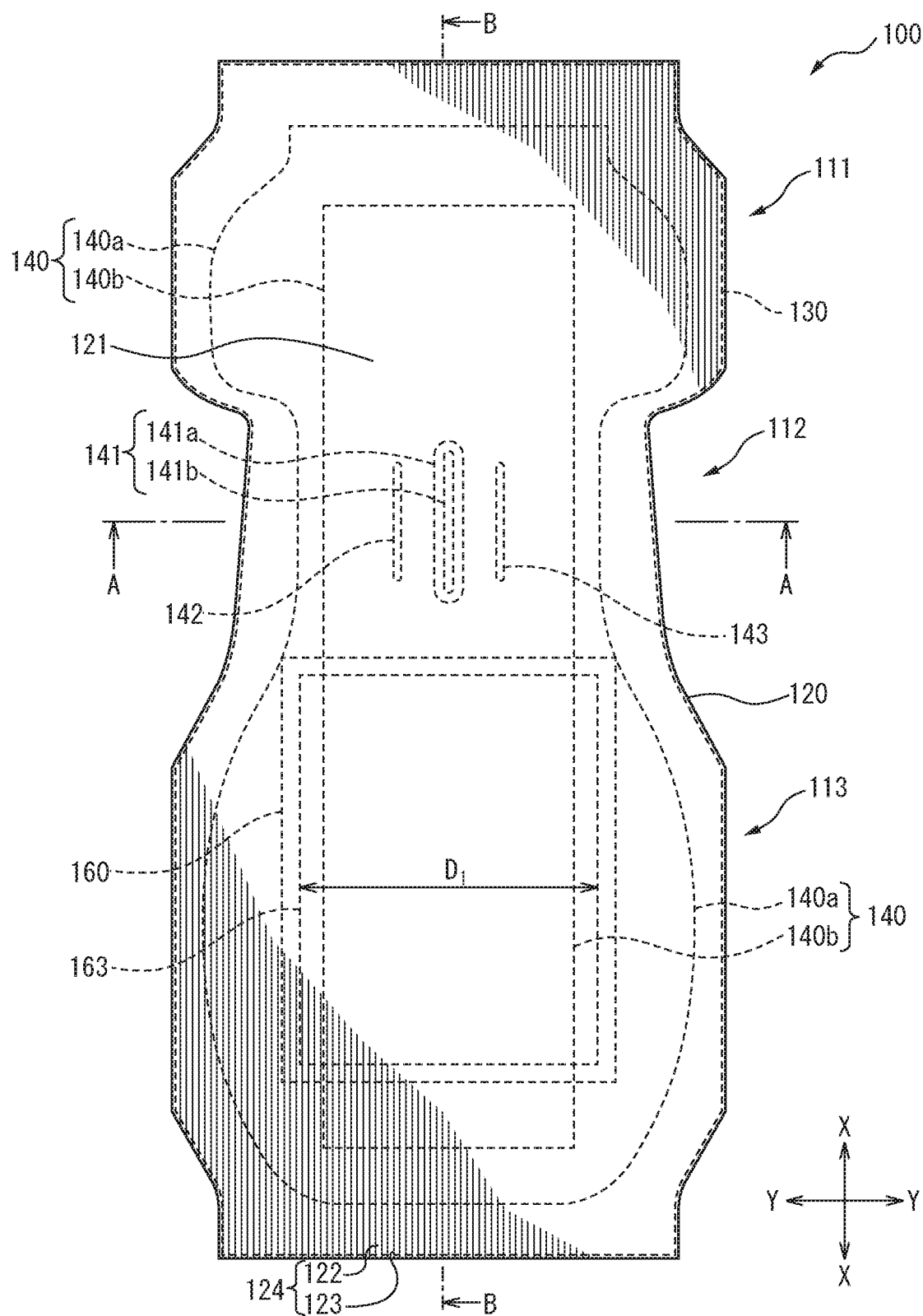
FIG. 1 is a plan view of a urine-absorbing pad according to an embodiment of the invention.

In the present specification, among both long sides, the proximal side to an imaginary center line extending in the widthwise direction through the center of the absorbent article will be referred to as "the inner side in the lengthwise direction", and the distal side will be referred to as "the outer side in the lengthwise direction". Also, among both sides in the widthwise direction, the proximal side to an imaginary center line extending in the lengthwise direction through the center of the absorbent article will be referred to as "the inner side in the widthwise direction", and the distal side will be referred to as "the outer side in the widthwise direction". In addition, among both sides in the thickness direction, the side in the thickness direction located on the skin side of the wearer will be referred to as the "skin side", and the other side in the thickness direction located on the clothing side of the wearer will be referred to as the "clothing side".

Aspects encompassed by the absorbent article of the present invention will be described below.

An absorbent article according to one aspect (hereinafter referred to as "aspect 1A") of the present invention is an absorbent article comprising a liquid-permeable top sheet, a liquid-impermeable back sheet, and a liquid-absorbing absorbent body disposed between the top sheet and the back sheet, and having a lengthwise direction, a widthwise direction, and a thickness direction that are mutually orthogonal; wherein the top sheet is a nonwoven fabric with a skin side surface on which protrusions are formed; and wherein the absorbent body has a through-hole penetrating through the absorbent body in the thickness direction or a recess that opens to a side of the top sheet.

The absorbent article according to aspect 1A can exert the following effects. Due to the force directed toward the inner side in the widthwise direction, that is applied when the absorbent article is worn, the skin side surface of the top sheet easily deforms into a projecting shape toward the clothing side (back sheet side) starting from a part (for example, a recess) other than the protrusions as a bending origin, while the absorbent body easily deforms into a projecting shape toward the skin side (top sheet side). Accordingly, when the absorbent article is worn, the top sheet easily enters into the through-hole or recess of the absorbent body. Consequently, even if the top sheet is pressed when the absorbent article is worn, a part of the top sheet at which the top sheet is entered into the through-hole or recess of the absorbent body is hardly pressed, and the shapes of the protrusions tend to be maintained at this part.

Urine of the elderly (especially a bedridden elderly person) contains more impurities than the urine of general adults. Accordingly, if the protrusions are collapsed and the volume and voids of the protrusions are reduced due to pressing of the top sheet, the impurities in the urine tend to remain more in the top sheet, thereby causing a reduction in liquid permeability of the top sheet. Concerning this point, in the adsorbent article of the aspect 1A, the volume and voids of the protrusions tend to be maintained, and accordingly the absorbent article is suitable as a urine-absorbing pad for absorbing the urine of the elderly (especially a bedridden elderly person). The term "elderly" generally means a person of 65 years or older.

In a preferred aspect (hereinafter referred to as "aspect 2A") of the absorbent article of aspect 1A, the protrusions are ridges extending in the lengthwise direction.

The absorbent article according to aspect 1A can exert the following effects.

Due to the force directed toward the inner side in the widthwise direction, that is applied when the absorbent article is worn, the skin side surface of the top sheet easily deforms into a projecting shape toward the clothing side (back sheet side) starting from a part (for example, a recess) other than the ridges as a bending origin. Accordingly, when the absorbent article is worn, the top sheet easily enters into the through-hole or recess of the absorbent body.

In a preferred aspect (hereinafter referred to as "aspect 3A") of the absorbent article according to aspect 1A or aspect 2A, the through-hole or recess extends in the lengthwise direction, through a center in the widthwise direction of the absorbent body.

The absorbent article according to aspect 3A can exert the following effects. Due to the force directed toward the inner side in the widthwise direction, that is applied when the absorbent article is worn, the absorbent body easily deforms into a projecting shape toward the skin side starting from the through-hole or recess as a bending origin. Accordingly, when the absorbent article is worn, the top sheet easily enters into the through-hole or recess of the absorbent body.

In a preferred aspect (hereinafter referred to as "aspect 3A") of the absorbent article according to aspect 1A or 2A, the absorbent body has a first layer and a second layer having a maximum width which is smaller than a minimum width of the first layer; and wherein the second layer is located nearer to the back sheet than the first layer.

The absorbent article according to aspect 4A can exert the following effects.

Due to the force directed toward the inner side in the widthwise direction, that is applied when the absorbent article is worn, the absorbent body easily deforms into a projecting shape toward the skin side starting from a part of the first layer, at which the first layer does not overlap the second layer, as a bending origin. Accordingly, when the absorbent article is worn, the top sheet easily enters into the through-hole or recess of the absorbent body.

According to a preferred aspect (hereinafter referred to as "aspect 5A") of the absorbent article of any of aspects 1A to 4A, the absorbent body has a compressed part which integrates the absorbent body in the thickness direction; and wherein the compressed part is formed on an outer side in the widthwise direction from the through-hole or recess.

The absorbent article according to aspect 5A can exert the following effects.

Due to the force directed toward the inner side in the widthwise direction, that is applied when the absorbent article is worn, the absorbent body easily deforms into a projecting shape toward the skin side starting from the compressed part as a bending origin. Accordingly, when the absorbent article is worn, the top sheet easily enters into the through-hole or recess of the absorbent body. Further, since the shape of the through-hole or recess of the absorbent body tends to be maintained, the space of the through-hole or recess for the top sheet to enter tends to be maintained.

According to a preferred aspect (hereinafter referred to as "aspect 6A") of the absorbent article of aspects 1A to 5A, a content of fibers oriented in the thickness direction at the protrusions of the nonwoven fabric is higher than a content of fibers oriented in the thickness direction at a section other than the protrusions of the nonwoven fabric.

The absorbent article according to aspect 6A can exert the following effects.

Due to the higher content of fibers oriented in the thickness direction at the protrusions, the volume and voids of the protrusions tend to be maintained, even if the top sheet is pressed when the absorbent article is worn. Accordingly, the absorbent article according to aspect 6A is especially suitable as an absorbent article (especially urine-absorbing pad) for absorbing the urine of the elderly (especially a bedridden elderly person).

According to a preferred aspect (hereinafter referred to as "aspect 7A") of the absorbent article of any of aspects 1A to 6A, the absorbent article further comprises a liquid-absorbing sheet having a liquid-permeable first sheet, a liquid-permeable second sheet, and an absorbent polymer layer disposed between the first sheet and the second sheet, wherein the liquid-permeable sheets is disposed between the top sheet and the absorbent body, and wherein the liquid-absorbing sheet is disposed so that the liquid-absorbing sheet does not overlap the through-hole or recess in the thickness direction.

The absorbent article according to aspect 7A can exert the following effects. When the absorbent polymer layer absorbs the liquid (for example, urine) supplied to the absorbent article and swells, the thickness of the absorbent polymer layer is increased. Accordingly, the swelled absorbent polymer layer functions as a pressure buffering layer, and protects a part of the top sheet at which the top sheet does not overlap the absorbent polymer layer in the thickness direction, from pressure. Consequently, the part of the top sheet at which the top sheet does not overlap the absorbent polymer layer is hardly pressed, and the shapes of the protrusions at this part tend to be maintained.

According to a preferred aspect (hereinafter referred to as "aspect 8A") of the absorbent article according to aspect 7A, the absorbent article has an abdomen side section, a crotch section and a back side section, aligned in the lengthwise direction; wherein the through-hole or recess is located in the crotch section; and wherein the liquid-absorbing sheet is located at the back side section. In another preferred aspect of the absorbent article according to aspect 7A, both edges of the absorbent polymer layer are located inside both edges of the first absorbing layer and outside both edges of the second absorbing layer in the widthwise direction of the absorbent article. The location of both edges of the absorbent polymer layer inside both edges of the first absorbing layer and outside both edges of the second absorbing layer can maximize the function as a pressure buffering layer for top sheet, across the region of top sheet in the widthwise direction thereof including at least the entire width of the second absorbing layer, and moreover can make the level difference due to the difference in size among the first absorbing layer, the second absorbing layer, and absorbent polymer layer even less noticeable by the wearer, even after the absorbent polymer layer absorbed a liquid and is swelled, thereby improving the wearing feeling of the absorbent article. When the absorbent article according to aspect 4A has the features of aspect 7A and further has the features wherein both edges of the absorbent polymer layer are located inside both edges of the first absorbing layer and outside both edges of the second absorbing layer in the widthwise direction of the absorbent article, the thickness of the absorbent article decreases from the center region at which the first absorbing layer and the second absorbing layer extend toward the outside, as can be seen from the positional relationship of the first and second absorbing layers indicated by projected contour lines in FIG. 1, and accordingly the level difference due to the difference in size of the first absorbing layer, the second absorbing layer, and absorbent polymer layer, especially the level difference due to the edges in the widthwise direction of the absorbent article which is thicker within the absorbent article, can be less noticeable by the wearer, even after the absorbent polymer layer absorbed a liquid and is swelled, thereby improving the wearing feeling.

The absorbent article according to aspect 8A can exert the following effects.

Due to the force directed toward the inner side in the widthwise direction, that is applied when the absorbent article is worn, a part of the top sheet, located at the crotch section, easily enters into the through-hole or recess of the absorbent body. Further, when the absorbent polymer layer of the liquid-absorbing sheet absorbs the liquid (for example, urine) supplied to the absorbent article and swells, the swelled absorbent polymer layer functions as a pressure buffering layer and protects a part of the top sheet, located at the back side section. Consequently, the shapes of the protrusions at the part of the top sheet, located in the crotch section tend to be maintained.

Aspects encompassed by the wearable article of the invention will now be described below.

A wearable article according to one aspect (hereinafter referred to as "aspect 1B") of the invention is a wearable article comprising an exterior body comprising a liquid-permeable top sheet with a mounting surface on which an absorbent article is to be mounted, and a liquid-impermeable back sheet, and having an abdomen side section, a crotch section, and a back side section; and the absorbent article according to any of aspects 1 to 8 mounted on the mounting surface in a detachable manner.

The wearable article of aspect 1B can exert the same function and effect as the absorbent article according to aspects 1A to 8A, depending on the aspect of the absorbent article mounted therein.

In a preferred aspect (hereinafter referred to as "aspect 2B") of the wearable article according to aspect 1B, the exterior body comprises a first leakage preventing section capable of rising up from the mounting surface and having an anchored edge which is anchored to the mounting surface and a free edge capable of being separated from the mounting surface; a first elastic member attached to the free edge of the first leakage preventing section in a stretched state, both sides of the first elastic member in a stretching direction are anchored to the mounting surface; a second leakage preventing section capable of rising up from the mounting surface and having an anchored edge which is anchored to the mounting surface and a free edge capable of being separated from the mounting surface; and a second elastic member attached to the free edge of the second leakage preventing section in a stretched state, both sides of the second elastic member in a stretching direction are anchored to the mounting surface; wherein the absorbent article is disposed on the mounting surface so that both edge sections of the absorbent article in the widthwise direction are respectively located between the mounting surface and the first leakage preventing section and between the mounting surface and the second leakage preventing section; wherein the adsorbent article is the adsorbent article according to aspect 7A or 8A; and wherein the absorbent polymer layer has a maximum width which is larger than the distance between the first elastic member and the second elastic member.

The wearable article according to aspect 2B can exert the following effects. When the absorbent polymer layer of the absorbent article absorbs a liquid and swells, the first and second leakage preventing sections are pushed up in the rising directions thereof. Accordingly, the first and second leakage preventing sections are hard to fall, and therefore the liquid leakage-preventing effects by the first and second leakage preventing sections can be effectively exerted.

There are no particular restrictions on the type and usage of the absorbent article of the invention. For example, absorbent articles include sanitary products such as urine-absorbing pads, disposable diapers, sanitary napkins and panty liners, which may be for humans or animals other than humans, such as pets. There are no particular restrictions on the fluid to be absorbed by the absorbent article of the invention, and for example, it may be liquid excreta (for example, urine, watery stool or menstrual blood) of the wearer.

Figure 2:
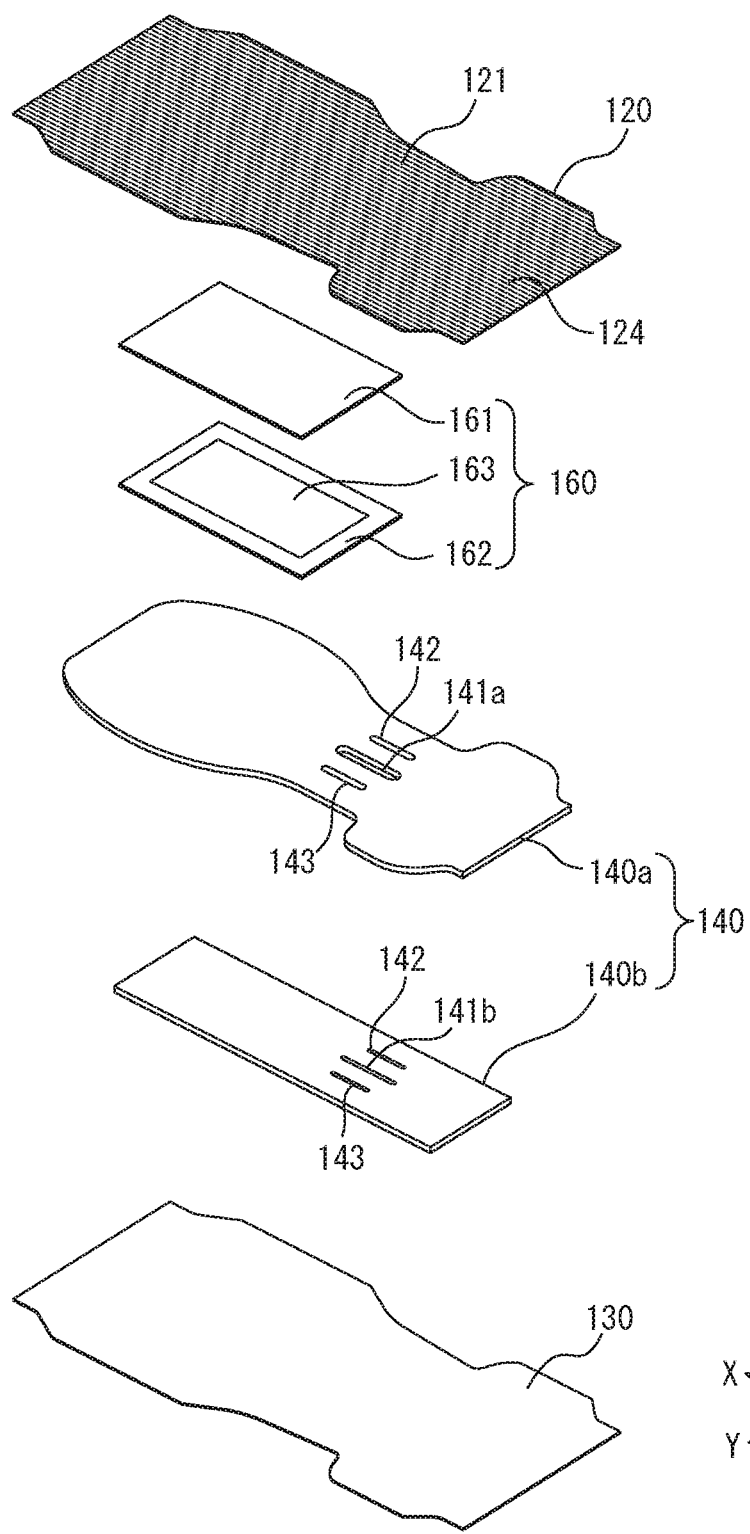
FIG. 2 is an exploded perspective view of the urine-absorbing pad shown in FIG. 1.
Figure 3:
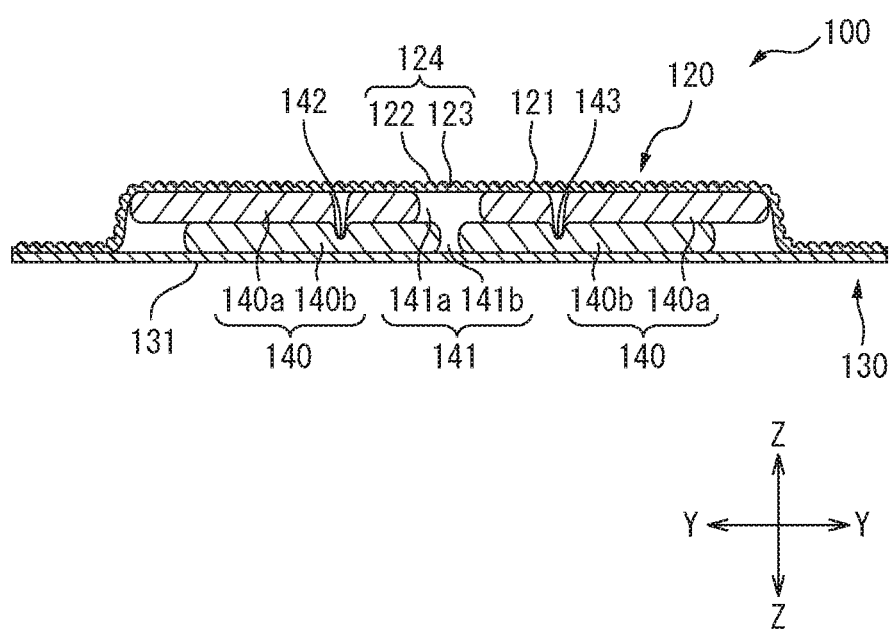
FIG. 3 is an end view along line A-A of FIG. 1.
Figure 5:
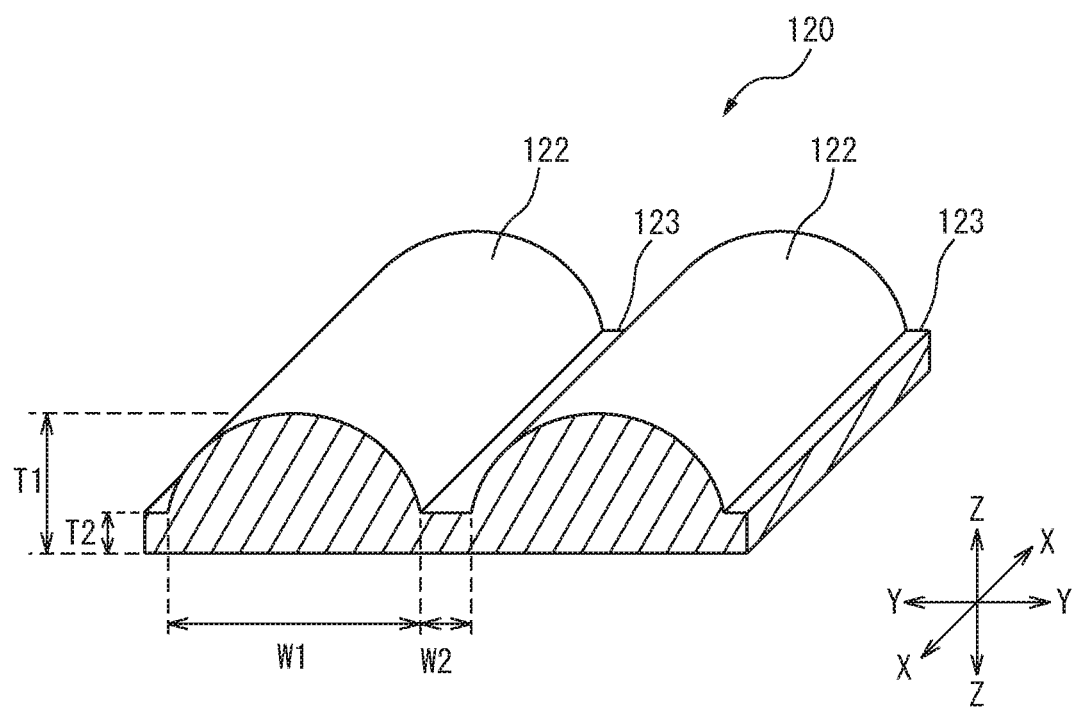
FIG. 5 is a partial magnified perspective view of the top sheet in the urine-absorbing pad shown in FIG. 1.

A urine-absorbing pad 100 will now be described as an embodiment of the absorbent article of the invention, with reference to FIGS. 1 to 5. FIG. 1 is a plan view of a urine-absorbing pad 100, FIG. 2 is an exploded perspective view of urine-absorbing pad 100, FIG. 3 is an end view along line A-A of FIG. 1, FIG. 4 is an end view along line B-B of FIG. 1, and FIG. 5 is a partial magnified perspective view of top sheet 120.

In its spread-out state, urine-absorbing pad 100 has a lengthwise direction X, a widthwise direction Y and a thickness direction Z that are mutually orthogonal.

Urine-absorbing pad 100 comprises a liquid-permeable top sheet 120 having a skin side surface 121, a liquid-impermeable back sheet 130 having a clothing side surface 131, and a liquid-absorbing absorbent body 140 disposed between top sheet 120 and back sheet 130.

Urine-absorbing pad 100 has an abdomen side section 111, a crotch section 112 and a back side section 113, aligned in lengthwise direction X. When urine-absorbing pad 100 is worn, abdomen side section 111 is in contact with the abdominal region of the wearer, crotch section 112 is in contact with the crotch region of the wearer, and back side section 113 is in contact with the gluteal region and/or the back region of the wearer. The length of urine-absorbing pad 100 is typically 350 to 880 mm, and the width is typically 160 to 460 mm.

Urine-absorbing pad 100 is worn in such a manner that skin side surface 121 of top sheet 120 is located on the skin side of the wearer and clothing side surface 131 of back sheet 130 is located on the clothing side of the wearer. Urine-absorbing pad 100 is preferably worn in a manner mounted in exterior body 200, described later. The shape of urine-absorbing pad 100, as viewed in a plan view, is a gourd-shape narrowed at approximately the center in the lengthwise direction X, and therefore the narrowed section of urine-absorbing pad 100 easily fits into the crotch of the wearer. Urine that has been discharged by the wearer penetrates into absorbent body 140 through top sheet 120, and is absorbed and held in absorbent body 140. Leakage of urine that has been absorbed and held by absorbent body 140 is prevented by back sheet 130.

The liquid-permeable sheet used for top sheet 120 is a nonwoven fabric. Examples of nonwoven fabrics include air-through nonwoven fabrics, spunbond nonwoven fabrics, point bond nonwoven fabrics, spunlace nonwoven fabrics, needle punching nonwoven fabrics and meltblown nonwoven fabrics, as well as combinations thereof (such as spunbond/melt blown/spunbond (SMS) nonwoven fabrics), but air-through nonwoven fabrics are preferred. The basis weight of the nonwoven fabric used as top sheet 120 is appropriately adjusted in consideration of the liquid permeability, feel on the skin and the like.

Ridges 122 (an example of the protrusions) are formed on skin side surface 121 of top sheet 120. Ridges 122 extend in lengthwise direction X and are aligned at a predetermined spacing in widthwise direction Y, with one groove 123 being located and formed between every two adjacent ridges 122. In other words, on skin side surface 121 there is formed a ridge-groove structure 124 comprising a plurality of ridges 122 extending in lengthwise direction X, and a plurality of grooves 123 extending in lengthwise direction X. In FIGS. 1 and 2, one ridge 122 is shown as the region between two adjacent lines, and one groove 123 is shown as a single line. Also, for simplicity, part of ridge-groove structure 124 formed in skin side surface 121 is omitted in FIG. 1. Furthermore, since line B-B shown in FIG. 1 is a line running through ridge 122, groove 123 does not appear in the end view on line B-B (FIG. 4).

This embodiment in which ridges 122 and grooves 123 extend continuously in almost straightly in lengthwise direction X is advantageous in that urine supplied to top sheet 120 easily spreads out in lengthwise direction X along ridges 122 and grooves 123, and spreading of urine in widthwise direction Y, and the consequent leakage of urine from urine-absorbing pad 100, can be prevented. However, the forms of ridges 122 and grooves 123 may be varied. As examples of modifications there may be mentioned an embodiment in which ridges 122 and grooves 123 extend in widthwise direction Y and are aligned in lengthwise direction X, an embodiment in which ridges 122 and grooves 123 extend while varying their directions (for example, in a wavy fashion), and an embodiment in which ridges 122 and grooves 123 extend intermittently in lengthwise direction X.

The surfaces of ridges 122 are curved, and the cross-sectional shapes of ridges 122 are nearly inverted U-shapes facing the surface. However, the cross-sectional shapes of ridges 122 may be varied. Examples of modifications include embodiments in which the cross-sectional shapes of ridges 122 are trapezoidal or triangular. Embodiments in which ridges 122 are tapered toward the top sections, including this embodiment, are advantageous in that the spaces of the grooves 123 are maintained even when ridges 122 are collapsed under force applied to urine-absorbing pad 100 (for example, body pressure by the wearer).

Ridges 122 have a thickness T1, and grooves 123 have a thickness T2. Thickness T1 of ridges 122 is typically 0.3 to 1.5 mm, preferably 0.6 to 1.4 mm, and more preferably 0.8 to 1.2 mm, and thickness T2 of grooves 123 is typically 0.1 to 0.5 mm, preferably 0.2 to 0.4 mm and more preferably 0.2 to 0.3 mm. Measurement of the thicknesses of the ridges and grooves is accomplished by the non-contact system described below, using a 100 mm×100 mm top sheet sample cut out from the urine-absorbing pad, and a laser displacement gauge (for example, a Series LJ-G High precision two-dimensional laser displacement gauge (model: LJ-G030) by Keyence Corp.). A sample of the top sheet is placed on a horizontal measuring stage and the displacements of five different ridges from the measuring stage are measured with a laser displacement gauge, recording the average value of the five measured values as the ridge thickness (mm). Similarly, the displacements of five different grooves from the measuring stage are measured with a laser displacement gauge, recording the average value of the five measured values as the groove thickness (mm).

Ridges 122 have width W1, and grooves 123 have width W2. Width W1 of ridges 122 is typically 2.0 to 5.0 mm and preferably 3.0 to 4.0 mm, and width W2 of grooves 123 is typically 1.0 to 3.0 mm and preferably 1.0 to 2.0 mm. The spacing between every two adjacent ridges 122 is typically equal to width W2 of the grooves, and the spacing between every two adjacent grooves 123 is typically equal to the width of ridges 122. Width W1 of ridges 122 is measured as the distance between the border lines between each ridge 122 and the two grooves 123 situated on either side of the ridge, based on a flat photograph or flat image of top sheet 120 in an unpressed state. The same applies for width W2 of grooves 123.

For this embodiment the thicknesses and widths of ridges 122 are substantially the same for every ridge, but a ridge having a different thicknesses and width from other ridges may be present. The same applies to the thicknesses and widths of grooves 122.

In the nonwoven fabric used as top sheet 120, the content of fibers oriented in the thickness direction in ridges 122 is preferably higher than the content of fibers oriented in the thickness direction in the sections of the nonwoven fabric other than ridges 122 (for example, grooves 123). The phrase "fibers oriented in the thickness direction" refers to fibers oriented at an angle of +45 degrees to −45 degrees with respect to thickness direction Z. The content of thickness oriented fibers in ridges 122 is preferably 55 to 100% and more preferably 60 to 100%. The difference between the content of thickness oriented fibers in ridges 122 and the content of fibers oriented in the thickness direction at sections of the nonwoven fabric other than ridges 122 (for example, grooves 123) is preferably 10 to 100% and more preferably 20 to 100%.

The measurement of the content of fibers oriented in the thickness direction in a predetermined section of the nonwoven fabric is as follows.

(1) The nonwoven fabric is cut to prepare a nonwoven fabric sample.

(2) A VHX-100 digital microscope by Keyence Corp. is used to photograph a magnified image of the cut surface of the nonwoven fabric sample from the perpendicular direction. The magnified image is an image magnified to a factor allowing 50 or more fibers to be measured, and the magnification factor may be 20× to 50×, for example. When the magnified image is taken, the focus is directed toward the foremost fibers in the cut surface of the nonwoven fabric sample (disregarding fibers that have irregularly protruded forward), for setting of the photographic depth. The magnified image is reproduced on a PC screen as a 3D image.

(3) The 3D image is converted to a 2D image, multiple lines extending parallel to the thickness direction of the nonwoven fabric sample are drawn on the 2D image, and the number of fibers oriented at angles of +45 degrees to −45 degrees with respect to the thickness direction of the nonwoven fabric sample is counted.

(4) The proportion of the number of counted fibers with respect to the total number of fibers in the measurement range is calculated.

(5) Steps (1) to (4) are repeated several times (for example, 3 to 5 times), and the average value is recorded as the content of fibers oriented in the thickness direction.

A nonwoven fabric in which ridge-groove structure 124 has been formed can be produced, for example, by forming a ridge-groove structure in a web containing thermoplastic resin fibers, and then subjecting it to heat treatment for heat fusion of the crossing sections between the thermoplastic resin fibers in the web. When an air-through nonwoven fabric is to be produced, the heat treatment is carried out by blasting hot air on the web.

The thermoplastic resin which constitutes the thermoplastic resin fibers in the web includes, for example, a polyolefin, polyester, polyamide, etc. Polyolefins include, for example, linear low-density polyethylene (LLDPE), low-density polyethylene (LDPE), medium-density polyethylene (MDPE), high-density polyethylene (HDPE), polypropylene, polybutylene, and copolymers composed mainly thereof (for example, ethylene-vinyl acetate copolymer (EVA), ethylene-ethyl acrylate copolymer (EEA), ethylene-acrylic acid copolymer (EAA), and ionomer resins). Polyesters include, for example, polyesters of a linear or branched polyhydroxyalkane acids having at most 20 carbon atoms, such as polyethylene terephthalate (PET), polytrimethylene terephthalate (PTT), polybutylene terephthalate (PBT), polylactic acid, and polyglycolic acid; copolymers composed mainly thereof; and copolymerized polyesters composed mainly of an alkylene terephthalate copolymerized with a small amount of another component. Polyamides include, for example, 6-nylon, 6,6-nylon, etc. The thermoplastic resin fiber is preferably hydrophilized. The hydrophilization treatment for the thermoplastic resin fiber include, for example, a treatment with a surfactant, hydrophilizing agent, etc. (for example, kneading of a surfactant into fibers, coating of the fiber surface with a surfactant, etc.), plasma treatment, etc.

The thermoplastic resin fibers may be composed of a single type of thermoplastic resin, but preferably they are composite fibers comprising two or more different thermoplastic resins. Preferred composite fibers are core-sheath composite fibers. The thermoplastic resin forming the sheath component of core-sheath composite fibers is selected as a thermoplastic resin with a melting point that is lower than the melting point of the thermoplastic resin forming the core component. Examples of thermoplastic resins forming the core component and sheath component of core-sheath composite fibers include olefin-based resins such as polyethylene and polypropylene, polyamide-based resins such as nylon, and polyester-based resins, and polyacrylonitrile-based resins. The thermoplastic resin forming the sheath component is preferably polyethylene (for example, high-density polyethylene, low-density polyethylene, linear low-density polyethylene, or a mixture of such types of polyethylene), and the thermoplastic resin forming the core component is preferably polypropylene or polyester.

The method used to form the ridge-groove structure in the web may be any of the methods described in, for example, Japanese Unexamined Patent Publication No. 2008-25079, Japanese Unexamined Patent Publication No. 2008-23326 and Japanese Unexamined Patent Publication No. 2009-30218. According to these methods, the web is placed on an air-permeable supporting member (for example, a net-like supporting member), and the air-permeable supporting member is moved in a predetermined direction while spraying a gas (typically air) continuously onto the top side of the web, to form a ridge-groove structure in the web. The bottom side of the web has a form following the form of the air-permeable supporting member. For example, when the web-mounting surface of a net-like supporting member is flat, the bottom side of the web will be substantially flat (and therefore the bottom side of the nonwoven fabric will also be substantially flat).

The region of the top side of the web on which the gas has been sprayed has grooves formed extending in the movement direction of the air-permeable supporting member, with ridges being formed between every two adjacent grooves. During this time, the fibers in the regions that have been sprayed with gas migrate to both sides of the grooves, so that the basis weight of the ridges will generally be higher than the basis weight of the grooves. In addition, the gas that has impacted the gas-impenetrable sections (for example, the wires) of the air-permeable supporting member and have been repelled causes the fibers in the web to curl upward, and the content of fibers oriented in the thickness direction at the ridges within the ridge-groove structure formed in the web is higher than the content of fibers oriented in the thickness direction at the other sections (for example, grooves). The number of ridges and grooves, as well as their spacing, basis weights, fiber densities, contents of fibers oriented in the thickness direction, etc. may be adjusted within the desired range by adjusting the number of nozzles, the orifice diameter and pitch, the temperature and spray volume of the gas sprayed from the nozzle, the tension of the web, and the like.

Figure 12A:
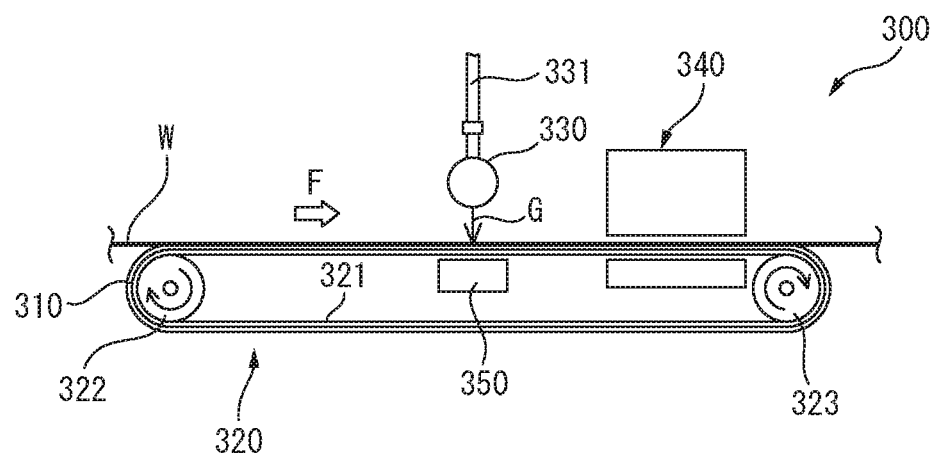
FIG. 12(A) is an overview of a nonwoven fabric production apparatus.
Figure 12B:
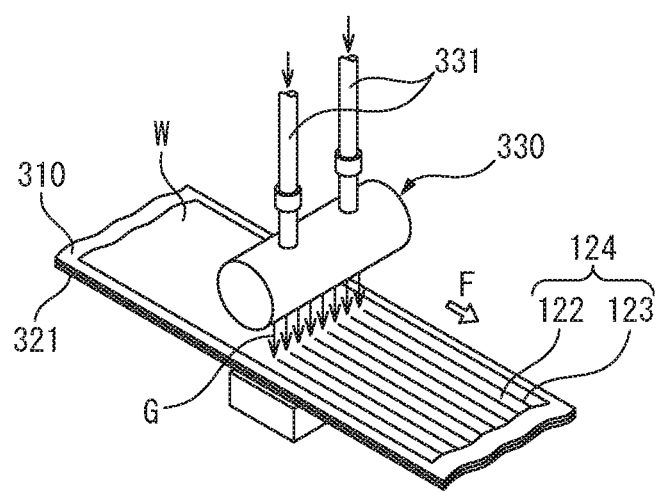
FIG. 12(B) is a magnified perspective view of the sprayer of a nonwoven fabric production apparatus.
Figure 13:
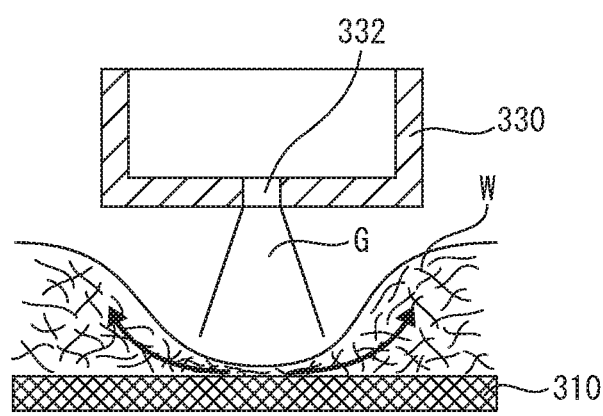
FIG. 13 is a diagram illustrating the action of gas sprayed from a sprayer onto a web.

FIGS. 12 and 13 are diagrams illustrating an embodiment of a nonwoven fabric production apparatus for production of a nonwoven fabric having a ridge-groove structure 124 formed therein. FIG. 12(A) is an overview of nonwoven fabric production apparatus 300, FIG. 12(B) is a magnified perspective view of sprayer 330 of nonwoven fabric production apparatus 300, and FIG. 13 is a diagram illustrating the action of gas sprayed from sprayer 330 onto web W.

Nonwoven fabric production apparatus 300 comprises an air-permeable supporting member 310 that supports web W, a conveyor 320 that conveys air-permeable supporting member 310 in a predetermined direction F, a sprayer 330 that sprays gas onto the surface of web W supported on air-permeable supporting member 310, and a heater unit 340 that performs heat treatment of web W after gas spraying treatment.

Air-permeable supporting member 310 is a net-like supporting member that is formed by interweaving a plurality of wires of a predetermined thickness, which form gas-impenetrable sections. By interweaving of the plurality of wires across predetermined spacings in air-permeable supporting member 310, a plurality of holes is formed as the gas-penetrable sections. The holes allow gas G sprayed from sprayer 330 to penetrate downward.

Conveyor 320 comprises a gas-permeable belt section 321 that supports air-permeable supporting member 310, and rotating parts 322, 323 that rotate gas-permeable belt section 321 in a predetermined direction.

Sprayer 330 is connected in a gas-flowable manner to a gas supply unit (not shown), via a gas supply pipe 331. A plurality of spray openings 332 are formed at predetermined spacings in sprayer 330. Gas G supplied from the gas supply unit (not shown) to sprayer 330 through gas supply pipe 331 is sprayed in a continuous manner on the top side of web W supported on air-permeable supporting member 310, from the plurality of spray openings 332 formed in sprayer 330. Gas G that has passed through air-permeable supporting member 310 is suctioned by an aspirator 350 disposed below sprayer 330.

Due to the collision of gas G sprayed from spray opening 332 with the gas-impenetrable sections (wires) of air-permeable supporting member 310, the fibers in web W curl upward, thereby improving the orientation of web W in the thickness direction (see FIG. 13). This results in a higher content of fibers oriented in the thickness direction at the ridges than the content of fibers oriented in the thickness direction at the grooves, within the ridge-groove structure formed in web W.

The temperature of gas G sprayed from spray opening 332 may be normal temperature, but from the viewpoint of improving the moldability of the ridge-groove structure, the temperature is preferably equal to or higher than the softening point of the thermoplastic resin fibers of web W, and preferably in the range of +50° C. to −50° C. from the melting point.

Web W supported on air-permeable supporting member 310 is subjected to heat treatment with a heater unit 340 after the gas spraying treatment. Web W supported on air-permeable supporting member 310 is continuously conveyed so as to reside for a predetermined time in the heating space formed inside heater unit 340. Heat treatment with the heater unit 340 causes heat fusion of the crossing sections between the thermoplastic resin fibers in web W while preserving the ridge-groove structure formed in web W, thereby producing a nonwoven fabric with a ridge-groove structure 124 formed therein.

Ridges 122 (the elevated sections extending in lengthwise direction X) for this embodiment are one example of the protrusions, and the types of protrusions formed on skin side surface 121 of top sheet 120 may be varied. As a modified example there may be mentioned an embodiment in which a nonwoven fabric having a skin side surface with a plurality of protrusions formed in an interspersed manner is used as top sheet 120. In a nonwoven fabric having a skin side surface with a plurality of protrusions formed in an interspersed manner, the thickness of the sections where the protrusions have been formed (the distance from the bottom side of the nonwoven fabric to the top sections of the protrusions), the thickness of sections (recesses) where the protrusions have not been formed (the distance from the bottom side of the nonwoven fabric to the deepest parts of the recesses), the pitch of the protrusions (the distance between the top sections of two adjacent protrusions), etc., are appropriately modified in consideration of the function of the irregular structure (for example, increasing the liquid permeability or improving the feel on the skin). The method of producing a nonwoven fabric having a skin side surface with a plurality of protrusions formed in an interspersed manner may be a method utilizing gear stretching, a method utilizing heat stretching of heat-extendable fibers and/or heat shrinkage of heat-shrinkable fibers, or the like. In a method utilizing heat stretching of heat-extendable fibers and/or heat shrinkage of heat-shrinkable fibers, the content of fibers oriented in the thickness direction at the ridges in the ridge-groove structure formed in the nonwoven fabric can potentially be higher than the content of fibers oriented in the thickness direction at the other sections (for example, the grooves).

An example of a method utilizing gear stretching is a method in which a first nonwoven fabric layer is shaped with protrusions and recesses by gear stretching, after which it is partially joined with a second nonwoven fabric layer at the sections other than the protrusions, to produce a nonwoven fabric having a skin side surface with a plurality of protrusions formed in an interspersed manner.

An example of a method of utilizing heat stretching of heat-extendable fibers and heat shrinkage of heat-shrinkable fibers is a method in which heat treatment is carried out on a laminated sheet having a heat-extendable fiber layer on the skin side and having a heat-shrinkable fiber layer partially joined to the heat-extendable fiber layer by joining sections, on the clothing side, and the heat-extendable fiber layer is caused to bulge on the skin side by heat stretching of the heat-extendable fiber layer and heat shrinkage of the heat-shrinkable fiber layer, thereby producing a nonwoven fabric having a skin side surface with a plurality of protrusions formed therein.

An example of a method utilizing heat shrinkage of heat-shrinkable fibers is a method in which heat treatment is carried out on a laminated sheet having a non-heat-shrinkable fiber layer on the skin side and having a heat-shrinkable fiber layer partially joined to the non-heat-shrinkable fiber layer by joining sections, on the clothing side, and the non-heat-shrinkable fiber layer is caused to bulge on the skin side by heat shrinkage of the heat-shrinkable fiber layer, thereby producing a nonwoven fabric having a skin side surface with a plurality of protrusions formed therein.

An example of a method utilizing heat stretching of heat-extendable fibers is a method in which heat treatment is carried out on a laminated sheet having a heat-extendable fiber layer on the skin side and having a non-heat-extendable fiber layer partially joined to the heat-extendable fiber layer by joining sections, on the clothing side, and the heat-extendable fiber layer is caused to bulge on the skin side by heat stretching of the heat-extendable fiber layer, thereby producing a nonwoven fabric having a skin side surface with a plurality of protrusions formed therein.

The liquid-impermeable sheets used as back sheet 130 includes, for example, waterproofed nonwoven fabrics (for example, point bond nonwoven fabrics, spunbond nonwoven fabrics, spunlace nonwoven fabrics, etc.), synthetic resin (for example, polyethylene, polypropylene, polyethylene terephthalate, etc.) films, composite sheets of a nonwoven fabric and a synthetic resin film, etc. The thickness, basis weight, etc. of side back sheet 130 are appropriately adjusted in consideration of the liquid impermeability, etc. Back sheet 130 is preferably air-permeable and moisture-permeable in addition to being liquid-impermeable, in order to reduce mustiness during wear.

Absorbent body 140 is disposed between top sheet 120 and back sheet 130, and extends from abdomen side section 111 through crotch section 112 up to back side section 113.

Absorbent body 140 has a first absorbing layer 140a and a second absorbing layer 140b. However, the number of layers of absorbent body 140 may be varied. As a modified example, there may be mentioned an embodiment in which absorbent body 140 is composed of a single layer, or an embodiment in which absorbent body 140 has one, two or more layers in addition to the first absorbing layer 140a and second absorbing layer 140b.

The first absorbing layer 140a and second absorbing layer 140b of absorbent body 140 contain an absorbent material capable of absorbing urine discharged from the wearer. The absorbent material includes, for example, hydrophilic fibers, absorbent polymers, etc. The hydrophilic fibers include, for example, wood pulp; non-wood pulp; regenerated celluloses such as rayon and fibril rayon; and semi-synthetic celluloses such as acetate and triacetate. The absorbent polymers include, for example, polyacrylic acid salt-based, polysulfonic acid salt-based, maleic anhydride salt-based, polyacrylamide-based, polyvinyl alcohol-based, and polyethylene oxide-based super-absorbent polymers (SAP), and the like.

The shape of the first absorbing layer 140a, as viewed in a plan view, is a gourd-shaped that is narrowed nearly at the center in the lengthwise direction, and the shape of the second absorbing layer 140b, as viewed in a plan view, is nearly rectangular. This will allow the narrowed section of absorbent body 140 to fit more easily in the crotch of the wearer. However, the shape of absorbent body 140 as viewed in a plan view may be varied.

The thickness, basis weight etc. of the first absorbing layer 140a and the second absorbing layer 140b are appropriately adjusted in consideration of the liquid absorbing and other properties of absorbent body 140. The first absorbing layer 140a has a thickness of typically 1.5 to 5.0 mm and preferably 2.5 to 3.5 mm, and a basis weight of typically 150 to 400 g/m$^2$ and preferably 200 to 300 g/m$^2$. The second absorbing layer 140b has a thickness of typically 1.5 to 5.0 mm and preferably 2.5 to 3.5 mm, and a basis weight of typically 150 to 400 g/m$^2$ and preferably 200 to 300 g/m$^2$. The measurement of the thickness of an absorbent body is carried out in the following manner, using a 100 mm×100 mm absorbent body sample cut from a urine-absorbing pad, and a commercially available thickness gauge (for example, a JA257 by Peacock, measuring surface: 50 mm (diameter), measuring pressure: 3 g/cm$^2$). The thickness gauge is pressed on 5 different locations of an absorbent body sample at a constant pressure of 3 g/cm$^2$, and the thickness at each location after 10 seconds of pressure is measured, recording the average value of the 5 measurements as the thickness (mm).

The maximum width of the second absorbing layer 140b, which is located nearer to back sheet 130 than the first absorbing layer 140a, is smaller than the minimum width of the first absorbing layer 140a. That is, absorbent body 140 has a high basis weight section formed by a region where the first absorbing layer 140a and the second absorbing layer 140b overlap with each other, low basis weight sections formed by regions of the first absorbing layer 140a at which the first absorbing layer 140a does not overlap the second absorbing layer 140b, and the low basis weight sections extend in lengthwise direction X. Incidentally, "high basis weight" and "low basis weight" mean relatively high and low basis weight. The widths of the first absorbing layer 140a and the second absorbing layer 140b may be varied.

In this embodiment in which the first absorbing layer 140a having a larger size is located nearer to top sheet 120 than the second absorbing layer 140b having a smaller size, the wearer hard to feel a level difference due to the difference in size between the first absorbing layer 140a and the second absorbing layer 140b, thereby improving the wearing feeling of the urine-absorbing pad 1 when it is worn. However, the positional relationship of the first absorbing layer 140a and the second absorbing layer 140b may be varied. An example of a modification is an embodiment in which the second absorbing layer 140b is located nearer to top sheet 120 than the first absorbing layer 140a.

The first absorbing layer 140a and second absorbing layer 140b may be covered by a core wrap. It is possible to prevent disintegration of the first absorbing layer 140a and second absorbing layer 140b by coating the first absorbing layer 140a and second absorbing layer 140b that are laminar molded articles of absorbent materials with a core wrap. The liquid-permeable sheet used as the core wrap includes, for example, a nonwoven fabric.

In the first absorbing layer 140a there is formed a through-hole 141 which penetrates through the first absorbing layer 140a in thickness direction Z, and in the second absorbing layer 140b there is formed through-hole 141b which penetrates through the second absorbing layer 140b in thickness direction Z. Through-holes 141a, 141b are located in crotch section 112 of urine-absorbing pad 100 and extend in lengthwise direction X through the center of absorbent 140 in widthwise direction Y. The first absorbing layer 140a and second absorbing layer 140b are layered in such a manner that the locations of through-holes 141a, 141b match with each other (that is, through-holes 141a, 141b are mutually communicating). Accordingly, in absorbent 140, through-hole 141 which penetrates through absorbent body 140 in thickness direction Z is formed by through-holes 141a, 141b. Similar to through-holes 141a, 141b, through-hole 141 is located in crotch section 112 of urine-absorbing pad 100 and extends in lengthwise direction X through the center of absorbent body 140 in widthwise direction Y. Consequently, the location of through-hole 141 easily matches with the location of the wearer's genital area (urinary excretion orifice), thereby improving the fitting properties of urine-absorbing pad 100 for the wearer. Moreover, the section that is in contact with the wearer's genital area (urinary excretion orifice) is hard to become moist, thereby preventing the wearer from feeling discomfort.

Instead of through-hole 141, there may be formed in absorbent body 140 a recess that opens to the side of top sheet 120. An absorbent body having a recess that opens to the side of top sheet 120 may be formed, for example, by layering the first absorbing layer with a through-hole 141a and a second absorbing layer without a through-hole 141b.

The lengths, widths, etc. of through-holes 141a, 141b are appropriately adjusted in consideration of the sizes, etc. of the first absorbing layer 140a and the second absorbing layer 140b. The width of through-hole 141a will generally be 5.0 to 50 mm and is preferably 10 to 20 mm. The width of through-hole 141b may be equal to or narrower than the width of through-hole 141a, and is typically 5.0 to 40 mm and preferably 10 to 15 mm. The length of through-hole 141a is typically 50 to 300 mm, and is preferably 50 to 200 mm and more preferably 50 to 150 mm. The length of through-hole 141b may be equal to or shorter than the length of through-hole 141a, and is typically 30 to 250 mm and preferably 30 to 150 mm. If the width and length of through-hole 141a are equal to or larger than the width and length of the through-hole 141b, the size of through-hole 141 will be kept essentially constant as viewed from the surface of top sheet 120 side of absorbent body 140, even with some shifting during the step of layering the first absorbing layer 140a and the second absorbing layer 140b. Furthermore, since a level difference is produced on the inner wall surface of through-hole 141, resulting in an increase in the inner surface area of through-hole 141, the urine-absorbing power of absorbent body 140 is improved at the section where through-hole 141 is formed.

In absorbent body 140, there are formed compressed portions 142, 143 that integrates absorbent body 140 in thickness direction Z, on the outer sides (both sides) of through-hole 141 in widthwise direction Y. Compressed portions 142, 143 integrate the first absorbing layer 140a and the second absorbing layer 140b in thickness direction Z. Compressed portions 142, 143 extend in lengthwise direction X in crotch section 112. Compressed portions 142, 143 are recesses that open to the side of top sheet 120, formed by heat embossing treatment.

Urine-absorbing pad 100 further comprises a liquid-absorbing sheet 160 disposed between top sheet 120 and absorbent body 140. Liquid-absorbing sheet 160 is disposed in the region from crotch section 112 to back side section 113, in such a manner so as not to overlap through-hole 141 in thickness direction Z.

Liquid-absorbing sheet 160 has liquid-permeable sheets 161, 162, and an absorbent polymer layer 163 disposed between liquid-permeable sheets 161, 162. Liquid-permeable sheets 161, 162 are nonwoven fabrics, for example. The nonwoven fabrics include the same examples as those mentioned for top sheet 120. The absorbent polymer contained in absorbent polymer layer 163 includes the same examples as those mentioned for absorbent body 140. The basis weight of absorbent polymer layer 163 is appropriately adjusted in consideration of the urine absorption, etc. desired for urine-absorbing pad 100. For example, when liquid-permeable sheets 161, 162 have a size of 180 mm×130 mm, 2 g of absorbent polymer which can absorb 60 g of physiological saline per 1 g may be used to form absorbent polymer layer 163 having a substantially the same size as liquid-permeable sheets 161, 162.

Absorbent polymer layer 163 has a maximum width $D_1$. The maximum width $D_1$ is the distance between an imaginary straight line extending in lengthwise direction X through the outermost point on one side in widthwise direction Y and an imaginary straight line extending in lengthwise direction X through the outermost point on the other side in widthwise direction Y, among the points on the contour line of absorbent polymer layer 163 in the plane perpendicular to thickness direction Z onto which absorbent polymer layer 163 is projected. For this embodiment, the width of absorbent polymer layer 163 is substantially constant.

Absorbent polymer layer 163 is anchored between liquid-permeable sheets 161, 162 by an adhesive (for example, a hot-melt adhesive) coated onto at least one of the surfaces of liquid-permeable sheets 161, 162. From the viewpoint of liquid permeability from liquid-absorbing sheet 160 to absorbent body 140, the adhesive is not coated over the entire interface between liquid-permeable sheets 161, 162, and for example, it is coated in a dotted, spiral, stripe or other pattern.

Absorbent polymer layer 163 may be segmented into a plurality of regions by regions in which the absorbent polymer is not present, extending in any desired direction.

Urine-absorbing pad 100 can exert the following effects.

Due to the force directed toward the inner side in widthwise direction Y, that is applied when the absorbent article is worn, skin side surface 121 of top sheet 120 easily deforms into a projecting shape toward the clothing side (back sheet 130 side) starting from a part (for example, groove 123) other than ridges 122 as a bending origin, while absorbent body 140 easily deforms into a projecting shape toward the skin side (top sheet 120 side) starting from through-hole 141, a part (low basis weight section) of the first absorbing layer 140a, at which the first absorbing layer 140a does not overlap the second absorbing layer 140b, and compressed parts 141, 142 as bending origins. Accordingly, when urine-absorbing pad 100 is worn, top sheet 120 easily enters into the through-hole or recess of absorbent body 140. Particularly, since through-hole 141 is located in crotch section 112, a part of top sheet 120, located at crotch section 112, easily enters into through-hole 141 of absorbent body 140. Consequently, even if top sheet 120 is pressed when urine-absorbing pad 100 is worn, a part of top sheet 120 at which top sheet 120 is entered into the through-hole 141 of absorbent body 140 is hardly pressed, and the shapes of ridges 122 tend to be maintained at this part.

Urine of the elderly (especially a bedridden elderly person) contains more impurities than the urine of general adults. Accordingly, if ridges 122 are collapsed and the volume and voids of ridges 122 are reduced due to pressing of top sheet 120, the impurities in the urine tend to remain more in top sheet 120, thereby causing a reduction in liquid permeability of top sheet 120. Concerning this point, in urine-absorbing pad 100, the volume and voids of ridges 122 tend to be maintained, and accordingly urine-absorbing pad 100 is suitable as a urine-absorbing pad for absorbing the urine of the elderly (especially a bedridden elderly person).

In the nonwoven fabric used as top sheet 120, if the content of fibers oriented in the thickness direction in ridges 122 is higher than the content of fibers oriented in the thickness direction in the sections (for example, grooves 123) other than ridges 122, even if top sheet 120 is pressed when urine-absorbing pad 100 is worn, the volume and voids of ridges 122 tend to be maintained. Consequently, urine-absorbing pad 100 is especially suitable as an absorbent article (especially a urine-absorbing pad) for absorbing the urine of the elderly (especially a bedridden elderly person).

When absorbent polymer layer 163 absorbs urine supplied to urine-absorbing pad 100 and swells, the thickness of absorbent polymer layer 163 is increased. Accordingly, swelled absorbent polymer layer 163 functions as a pressure buffering layer, and protects a part of top sheet 120 at which top sheet 120 does not overlap absorbent polymer layer 163 in thickness direction Z, from pressure. In particular, since liquid-absorbing sheet 160 is disposed so as not to overlap through-hole 141 in thickness direction Z, the part of top sheet 120 at which top sheet 120 overlaps through-hole 141 in thickness direction Z is protected from pressure. Consequently, the part of top sheet 120 at which top sheet 120 overlaps through-hole 141 in thickness direction Z is hardly pressed, and the shapes of ridges at this part tend to be maintained.

Figure 7:
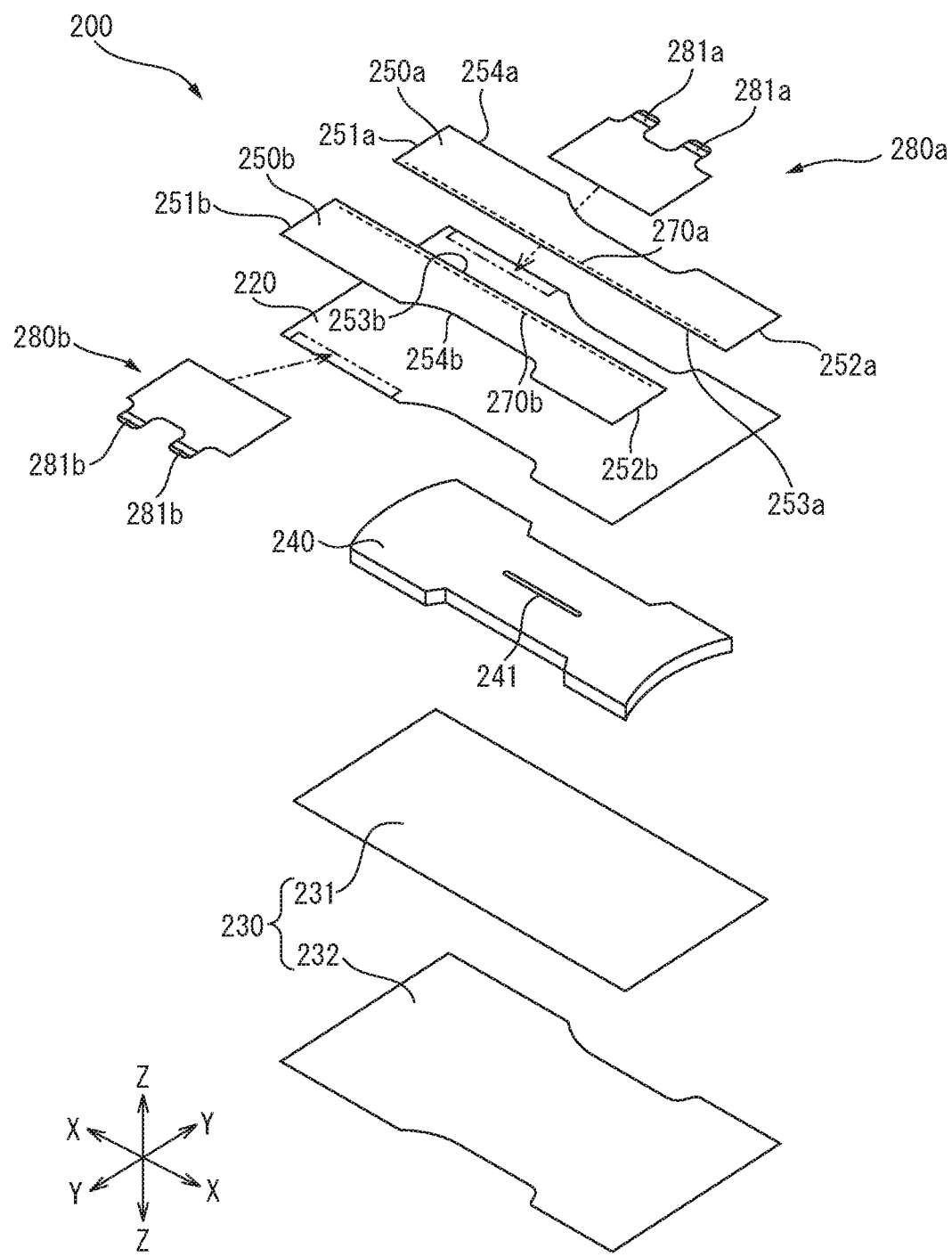
FIG. 7 is an exploded perspective view of the exterior body shown in FIG. 6.
Figure 8:
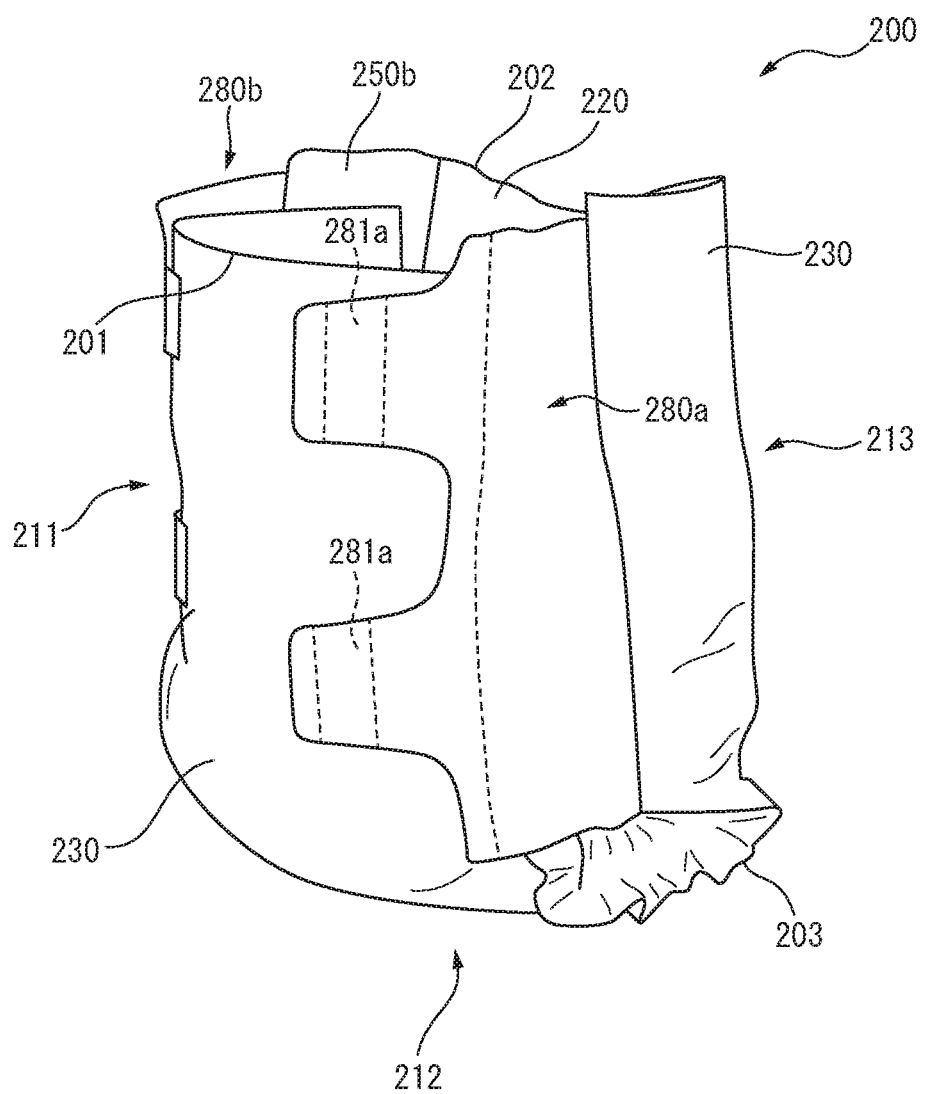
FIG. 8 is a perspective view showing the state of the exterior body of FIG. 6, deformed into the shape of underwear.
Figure 9:
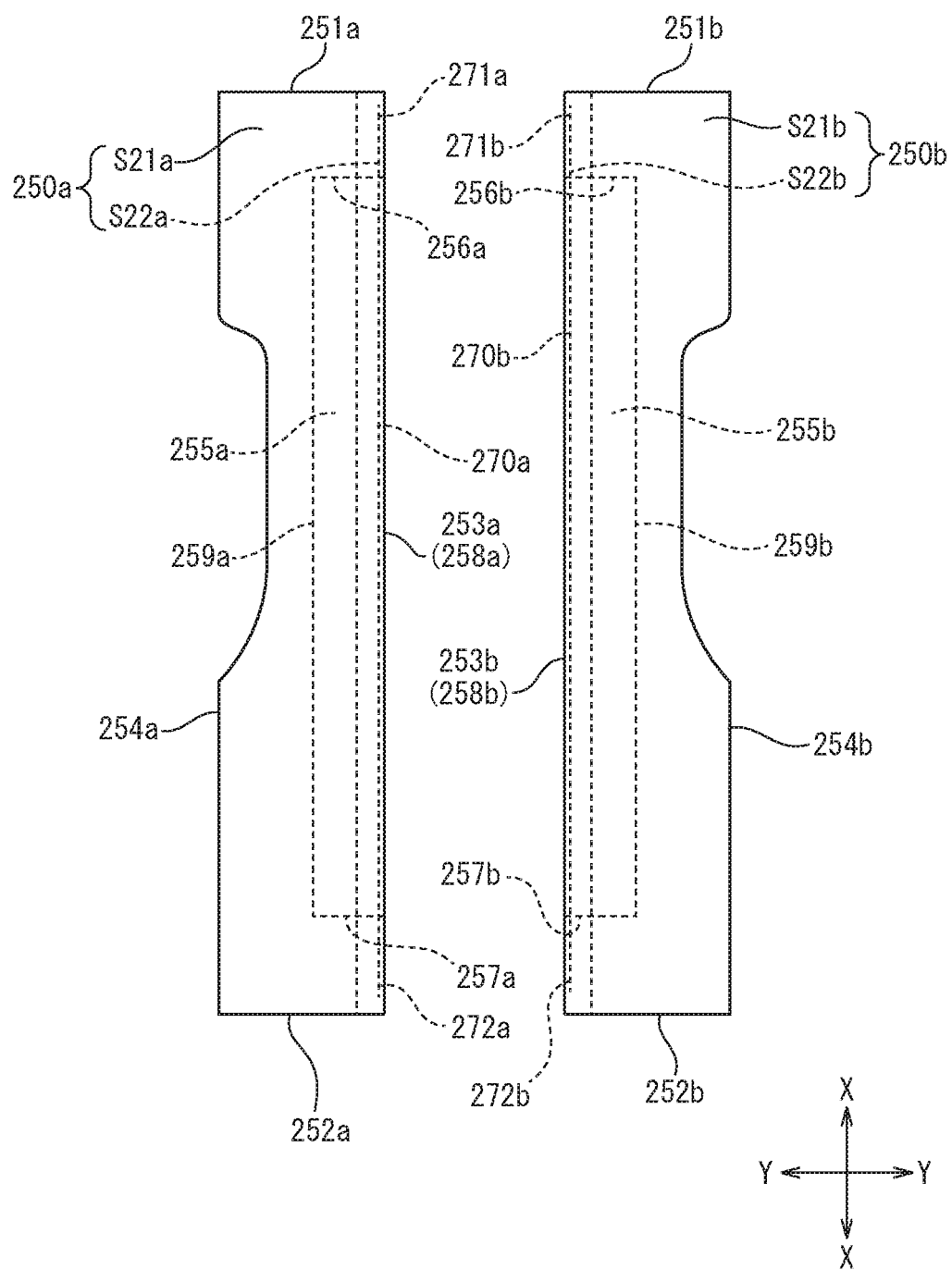
FIG. 9 is a drawing illustrating a side sheet in the exterior body shown in FIG. 6.

Exterior body 200 according to one embodiment of an exterior body of the invention will now be described based on FIGS. 6 to 9. FIG. 6 is a plan view of exterior body 200, FIG. 7 is an exploded perspective view of exterior body 200, FIG. 8 is a perspective view of exterior body 200 deformed into a shape of underwear, and FIG. 9 is an illustration of side sheets 250a, 250b of exterior body 200.

In its spread-out state, exterior body 200 has a lengthwise direction X, a widthwise direction Y, and a thickness direction Z that are mutually orthogonal. The lengthwise direction X, widthwise direction Y and thickness direction Z of the exterior body 200 correspond to lengthwise direction X, widthwise direction Y, and thickness direction Z of urine-absorbing pad 100.

Exterior body 200 comprises body section 210 having both edges 201, 202 in lengthwise direction X and both edges 203, 204 in widthwise direction Y, and side flap sheets 280a, 280b extending in widthwise direction Y from both edges 203, 204 in widthwise direction Y of body section 210.

Body section 210 has an abdomen side section 211, a crotch section 212, and a back side section 213, aligned in the lengthwise direction X. The abdomen side section 211 is the section which is in contact with the abdominal region of the wearer, the crotch section 212 is the section which is in contact with the crotch region of the wearer, and back side section 213 is the section which is in contact with the gluteal region and/or the back region of the wearer. The length of body section 210 is typically 650 to 1000 mm, and the width is typically 300 to 690 mm.

A pair of side flap sheets 280a, 280b are provided on either side of back side section 213 of body section 210. When both edges in widthwise direction Y of abdomen side section 211 and both edges in widthwise direction Y of back side section 213 are engaged by hook sections 281a, 281b of a mechanical fastener, as engagement means mounted on side flap sheets 280a, 280b, exterior body 200 is formed into the shape of underwear, while a waist opening is formed by both edges 201, 202 in lengthwise direction X of body section 210, and leg openings are formed by both edges 213, 214 in widthwise direction Y of body section 210 (see FIG. 8).

Exterior body 200 can be deformed from its developed form into an underwear form, but alternatively, it may be initially shaped into an underwear form. For example, by joining both edges in widthwise direction Y of crotch region 212 and both edges in widthwise direction Y of back side section 213, it is possible to shape exterior body 200 into an underwear form. In this case, the pair of side flap sheets 280a, 280b may be omitted.

Body section 210 is a gourd-shape which is narrowed nearly at the center section in lengthwise direction X (the section corresponding to crotch section 212). Accordingly, crotch section 212 is easily fit into the crotch of the wearer. However, the shape of body section 210 may be appropriately varied in a range that allows deformation into an underwear form.

Body section 210 comprises a liquid-permeable top sheet 220 having a skin side surface 221, a liquid-impermeable back sheet 230 having a clothing side surface 231, a liquid-absorbing absorbent body 240 disposed between the top sheet 220 and the back sheet 230, and liquid-impermeable side sheets 250a, 250b disposed at both edge sections in widthwise direction Y of skin side surface 221 of the top sheet 220. However, absorbent body 240 may be omitted.

The liquid-permeable sheet used for top sheet 220 is, for example, a nonwoven fabric. The nonwoven fabric may be any of the same examples mentioned for top sheet 120. The basis weight, thickness, etc. of top sheet 220 are appropriately adjusted in consideration of the liquid permeability, feel on the skin and the like.

Back sheet 230 has a liquid-impermeable sheet 231 located on the skin side and a liquid-impermeable sheet 232 located on the clothing side. Liquid-impermeable sheets 231, 232 include, for example, waterproofed nonwoven fabrics, synthetic resin films, and composite sheets of nonwoven fabrics and synthetic resin films. The thickness, basis weight, etc. of back sheet 230 are appropriately adjusted in consideration of the liquid impermeability and the like. Back sheet 230 is preferably air-permeable and moisture-permeable in addition to being liquid-impermeable, in order to reduce mustiness during wear.

Absorbent body 240 is disposed between top sheet 200 and back sheet 300, and extends from abdomen side section 211 through crotch section 212 up to back side section 213. The shape of absorbent body 240, as viewed in a plan view, is a gourd-shape which is narrowed nearly at the center in lengthwise direction X. This will allow the narrowed section of absorbent body 240 to fit more easily in the crotch of the wearer. Absorbent body 240a contains an absorbent material capable of absorbing urine discharged by the wearer. The absorbent material includes the same examples as those mentioned for absorbent article 140. Absorbent body 240 may also be covered by a core wrap. The thickness, basis weight, etc. of absorbent body 240 are appropriately adjusted in consideration of the liquid absorption properties and the like. The thickness of absorbent body 240 is typically 3 to 10 mm and preferably 4 to 7 mm, and the basis weight is typically 150 to 500 g/m² and preferably 200 to 400 g/m².

In absorbent body 240 there is formed through-hole 241 which penetrates through absorbent body 240 in thickness direction Z. Through-hole 241 is located in crotch section 212 of exterior body 200 and extends in lengthwise direction X through the center of absorbent body 240 in widthwise direction Y. Consequently, the location of through-hole 141 of urine-absorbing pad 100 is easily matched with the location of through-hole 241 of exterior body 200 when mounting urine-absorbing pad 100 in exterior body 200.

Instead of through-hole 241, there may be formed in absorbent body 240 a recess which opens to the side of top sheet 220. An absorbent body having a recess which opens to the side of top sheet 220 may be formed, for example, by layering a first absorbing layer with through-hole 241 and a second absorbing layer without through-hole.

The lengths, widths, etc. of through-hole 241 are appropriately adjusted in consideration of the size, etc. of absorbent body 240. The width of through-hole 241 may be equal to or wider than the width of through-hole 141, and is typically 5 to 50 mm and preferably 15 to 25 mm. The length of through-hole 241 may be equal to or longer than the length of through-hole 141, and is typically 50 to 700 mm and preferably 90 to 350 mm. Since the width and length of through-hole 241 are equal to or greater than the width and length of through-hole 141, the location of through-hole 141 of urine-absorbing pad 100 is easily matched with the location of through-hole 241 of exterior body 200 when mounting urine-absorbing pad 100 in exterior body 200.

The liquid-impermeable sheets used as side sheets 250a, 250b include, for example, waterproofed nonwoven fabrics (for example, point bond nonwoven fabrics, spunbond nonwoven fabrics, spunlace nonwoven fabrics, etc.), synthetic resin (for example, polyethylene, polypropylene, polyethylene terephthalate, etc.) films, composite sheets of nonwoven fabrics and synthetic resin films, etc. The thickness, basis weight, etc. of side sheets 250a, 250b are appropriately adjusted in consideration of the liquid impermeability, etc.

Side sheet 250a has both edges 251a, 252a in lengthwise direction X and both edges 253a, 254a in widthwise direction Y, while side sheet 250b has both edges 251b, 252b in lengthwise direction X and both edges 253b, 254b in widthwise direction Y. Side sheets 250a, 250b have leakage preventing sections 255a, 255b as portions thereof. Leakage preventing section 255a has both edges 256a, 257a in lengthwise direction X and both edges 258a, 259a in widthwise direction Y, while leakage preventing section 255b has both ends 256b, 257b in lengthwise direction X and both ends 258b, 259b in widthwise direction Y. Edges 253b, 253b of side sheets 250a, 250b are located nearer than edges 254a, 254b to the imaginary center line extending in lengthwise direction X through the center in widthwise direction Y of skin side surface 221 of top sheet 220. Edges 253a, 253b of side sheets 250a, 250b will also be referred to hereunder as "proximal edges" and edges 254a, 254b as "distal edges". Similarly, edges 258a, 258b of leakage preventing sections 255a, 255b will also be referred to as "proximal edges" and edges 259a, 259b as "distal edges".

Leakage preventing sections 255a, 255b are formed within the regions of side sheets 250a, 250b overlapping with top sheet 220 in thickness direction Z, and proximal edges 258a, 258b of leakage preventing sections 255a, 255b match with proximal edges 253a, 253b of side sheets 250a, 250b.

In the regions of side sheets 250a, 250b at which side sheets 250a, 250b overlap top sheet 220 in thickness direction Z, leakage preventing sections 255a, 255b are not anchored to skin side surface 221 of top sheet 220, but the sections other than leakage preventing sections 255a, 255b are anchored to skin side surface 221 of top sheet 220. Consequently, both edges and distal edges 259a, 259b of leakage preventing sections 255a, 255b in lengthwise direction X constitute the anchored edges anchored to skin side surface 221 of top sheet 220, while proximal edges 258a, 258b of leakage preventing sections 250a, 250b are not anchored to skin side surface 221 of top sheet 220 and serve as free edges capable of being separated from skin side surface 221 of top sheet 220. The manner of joining side sheets 250a, 250b and top sheet 220 may be, for example, joining by a hot-melt adhesive.

Side sheets 250a, 250b have first sheet sections S21a, S21b extending in widthwise direction Y from distal edges 254a, 254b to proximal edges 253a, 253b, and second sheet sections S22a, S22b joined to the first sheet sections S21a, S21b, being folded over to the side of top sheet 220 at proximal edges 253a, 253b. Between the first sheet section S21a and the second sheet section S22a of side sheet 250a, an elastic member 270a extending in lengthwise direction X along proximal edge 253a is mounted in a contractible manner in a stretched state, and between the first sheet section S21b and the second sheet section S22b of side sheet 250b, an elastic member 270b extending in lengthwise direction X along proximal edge 253b is mounted in a contractible manner in a stretched state. The stretching directions of the elastic members 270a, 270b approximately match lengthwise direction X. Both ends 271a, 272a of elastic member 270a in lengthwise direction X (stretching direction) extend in lengthwise direction X beyond both edges 256a, 257a in lengthwise direction X of leakage preventing section 255a, while both edges 271b, 272b of elastic member 270b in lengthwise direction X (stretching direction) extend in lengthwise direction X beyond both edges 256b, 257b in lengthwise direction X of leakage preventing section 255b. Also, both edges 271a, 272a of elastic member 270a in lengthwise direction X (stretching direction) are anchored to top sheet 220 while being sandwiched between the first sheet section S21a and the second sheet section S22a, and both ends 271b, 272b of elastic member 270b in lengthwise direction X (stretching direction) are anchored to top sheet 220 while being sandwiched between the first sheet section S21b and second sheet section S22b. As a result, leakage preventing sections 255a, 255b are capable of rising up from skin side surface 221 of top sheet 220 by the contractive force of elastic members 270a, 270b. When leakage preventing sections 255a, 255b rise up from skin side surface 221 of top sheet 220, three-dimensional gather sections are formed. When leakage preventing sections 255a, 255b rise up, distal edges 259a, 259b form base sections, and the proximal edges 258a, 258b separate from skin side surface 221 of top sheet 220, moving toward the skin side of the wearer. Elastic members 270a, 270b include, for example, rubber thread, flat rubber, and the like.

In exterior body 200, skin side surface 221 of top sheet 220 serves as the mounting surface for mounting of urine-absorbing pad 100. Urine-absorbing pad 100 can be mounted in a detachable manner into skin side surface 221 of top sheet 220.

Figure 10:
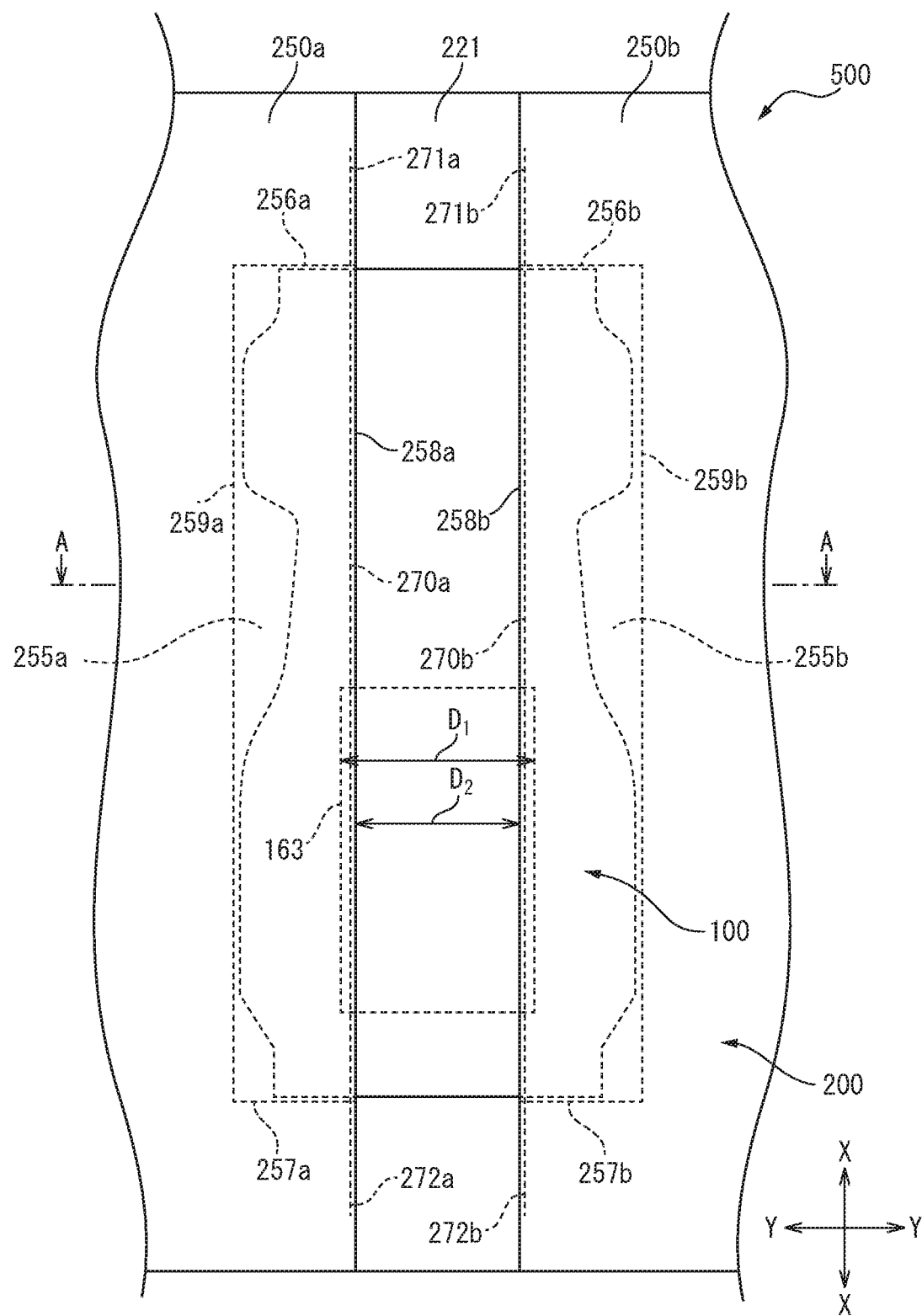
FIG. 10 is a partial enlarged plan view of a wearable article according to an embodiment of the invention.

A wearable article 500 according to an embodiment of the wearable article of the present invention will now be described based on FIGS. 10 and 11. FIG. 10 is a partial enlarged plan view of wearable article 500, and FIG. 11 is a cross-sectional view along line A-A of FIG. 10.

Wearable article 500 comprises an exterior body 200, and a urine-absorbing pad 100 mounted in a detachable manner on the mounting surface (skin side surface 221 of the top sheet 220) of the exterior body 200.

Urine-absorbing pad 100 is disposed on the mounting surface of the exterior body 200 in such a manner that both edge sections of urine-absorbing pad 100 in widthwise direction Y are located between the mounting surface (skin side surface 221 of top sheet 220) of the exterior body 200 and leakage preventing sections 225a, 255b. When urine-absorbing pad 100 is mounted into the exterior body, ridge-groove structure 124 formed on top sheet 120 of urine-absorbing pad 100 serves as a marking allowing for easy positioning of lengthwise direction X of urine-absorbing pad 100 and lengthwise direction X of exterior body 200.

Maximum width $D_1$ of absorbent polymer layer 163 of urine-absorbing pad 100 is greater than spacing $D_2$ between elastic member 270a and elastic member 270b. When absorbent polymer layer 163 absorbs urine supplied to urine-absorbing pad 100 and swells, leakage preventing sections 255a, 255b are pushed upward in the direction in which they rise. Accordingly, the three-dimensional gather sections formed by rising of leakage preventing sections 255a, 255b are resistant to collapse, and the urine leakage-preventing effect of the three-dimensional gather sections is effectively exerted.

Spacing $D_2$ between elastic member 270a and elastic member 270b is the spacing between a first imaginary line extending along the mounting surface through both edges 271a, 272a in lengthwise direction X of elastic member 270a, and a second imaginary line extending along the mounting surface through both edges 271b, 272b in lengthwise direction X of elastic member 270b. Both edges of elastic members 270a, 270b in lengthwise direction X are disposed so as to be substantially parallel to the first imaginary line and the second imaginary line.

Both edges of leak-proof sections 255a, 255b in lengthwise direction X may also approximately match both edges of urine-absorbing pad 100 in the lengthwise direction. The three-dimensional gather sections formed by rising of leak-proof sections 255a, 255b are resistant to collapse, and the urine leakage-preventing effect of the three-dimensional gather sections is effectively exerted.

Through-hole 141 formed in absorbent body 140 of urine-absorbing pad 100 overlaps through-hole 241 formed in absorbent body 240 of exterior body 200, in thickness direction Z. Consequently, even if top sheet 120 is pressed when wearable article 500 is worn, a part of top sheet 120 at which top sheet 120 is entered into through-hole 141 of absorbent body 140 is hardly pressed, and the shapes of ridges 122 tend to be maintained at this part.

EXAMPLES

Example 1

(1) Production of Web

A web was produced as a layered body of a first fiber layer and a second fiber layer.

A concentric core-sheath composite fiber A having polyethylene terephthalate as the core component and polyethylene as the sheath component, coated with a hydrophilizing oil agent for durable hydrophilicity, was used as the fiber of the first layer. Fiber A had a mean fineness of 2.2 dtex and a mean fiber length of 45 mm.

A mixture of a concentric core-sheath composite fiber B having polyethylene terephthalate as the core component and polyethylene as the sheath component, coated with a hydrophilizing oil agent for initial hydrophilicity, and an eccentric core-sheath composite fiber C having polyethylene terephthalate as the core component and polyethylene as the sheath component, coated with a hydrophilizing oil agent for durable hydrophilicity (mass ratio: 1:1) was used as the fiber of the second layer. Fiber B had a mean fineness of 3.3 dtex and a mean fiber length of 38 mm. Fiber C had a mean fineness of 2.2 dtex and a mean fiber length of 44 mm.

A web was produced as a layered body of a first fiber layer (basis weight: 20 g/m$^2$) and a second fiber layer (basis weight: 10 g/m$^2$), using a carding machine at a speed of 20 m/min. A gas spraying treatment was carried out on the surface of the first layer.

(2) Production of Nonwoven Fabric

The web produced in (1) above and the nonwoven fabric production apparatus 300 shown in FIG. 12 were used to produce a nonwoven fabric having a skin side surface with a ridge-groove structure formed therein.

The settings for the nonwoven fabric production apparatus 300 were as follows.
Diameter of spray opening 332: 1.0 mm (circular)
Pitch of spray opening 322: 3.0 mm
Spray gas temperature: 310° C.
Spray gas airflow rate per spray opening: 5 L/min
Web transport speed: 100 m/min
Air-permeable supporting member 310 (net-like supporting member): 70 mesh
Heat treatment with heater unit 340: Treatment for 6 seconds with a heat treatment temperature of 140° C., and a through-wind speed of 1.2 m/sec.

Comparative Example 1

(1) Production of Web

A web was produced as a layered body of a first layer and a second layer.

A mixture of a concentric core-sheath composite fiber D having polyethylene terephthalate as the core component and polyethylene as the sheath component, coated with a hydrophilizing oil agent for durable hydrophilicity, and an eccentric core-sheath composite fiber E having polyethylene terephthalate as the core component and polyethylene as the sheath component, coated with a hydrophilizing oil agent for durable hydrophilicity (mass ratio: 1:1) was used as the fiber of the first layer. Fiber D had a mean fineness of 2.2 dtex and a mean fiber length of 45 mm. Fiber E had a mean fineness of 2.2 dtex and a mean fiber length of 44 mm.

A concentric core-sheath composite fiber F having polyethylene terephthalate as the core component and polyethylene as the sheath component, coated with a hydrophilizing oil agent for initial hydrophilicity, was used as the fiber of the second layer. Fiber F had a mean fineness of 2.8 dtex and a mean fiber length of 44 mm.

A web was produced as a layered body of a first fiber layer (basis weight: 10 g/m$^2$) and a second fiber layer (basis weight: 20 g/m$^2$), using a carding machine at a speed of 20 m/min.

(2) Production of Nonwoven Fabric

A nonwoven fabric was produced using the web produced in (1) above, in the same manner as Example 1 except that the gas spraying treatment with the sprayer 330 was not carried out.

Test Example 1

The dry thicknesses and wet thicknesses of the nonwoven fabrics produced in Example 1 and Comparative Example 1 were measured.

The method for measuring the dry thickness and wet thickness of each nonwoven fabric is described above.

The nonwoven fabric produced in Example 1 had a dry thickness of 0.86 mm and a wet thickness of 0.79 mm. The wet thickness corresponded to 91% of the dry thickness.

The nonwoven fabric produced in Comparative Example 1 had a dry thickness of 0.78 mm and a wet thickness of 0.62 mm. The wet thickness corresponded to 80% of the dry thickness.

[Test Example 2] Measurement of Urine Absorption Time

The urine absorption time was measured using a commercially available urine-absorbing pad without a ridge-groove structure formed on the skin side surface of the top sheet (comparison product), and a urine-absorbing pad having the same construction as the comparison product except for using the nonwoven fabric produced in Example 1 as the top sheet (invention product). The urine samples used were urine samples A, B and C, taken from bedridden elderly individuals A, B and C.

A cylinder with a 60 mm diameter was placed on the urine-absorbing pad, and 80 mL of the urine sample was injected into the cylinder at an injection rate of 10 mL/sec. The time after the start of injection until the urine residing in the cylinder disappeared was measured, and was recorded as the 1st urine absorption time (sec).

At 5 minutes after the start of injection of the first urine sample, a load of 200 g was applied to the cylinder and 80 mL of urine sample was injected at an injection rate of 10 mL/sec (2nd time). The time after the start of the second injection until the urine residing in the cylinder disappeared was measured, and was recorded as the 2nd urine absorption time (sec).

At 10 minutes after the start of injection of the first urine sample, a load of 200 g was applied to the cylinder and 80 mL of urine sample was injected at an injection rate of 10 mL/sec (3rd time). The time after the start of third injection until the urine residing in the cylinder disappeared was measured, and was recorded as the 3rd urine absorption time (sec).

When the comparison product was used, the first, second and third absorption times for general adult urine were 10 seconds, 16 seconds and 23 seconds, respectively, whereas the first, second and third absorption times for urine sample A were 10 seconds, 31 seconds and 72 seconds, respectively, the first, second and third absorption times for urine sample B were 10 seconds, 34 seconds and 125 seconds, respectively, and the first, second and third absorption times for urine sample C were 15 seconds, 57 seconds and 153 seconds, respectively. When urine was repeatedly absorbed with the comparison product, the urine absorption time increased notably. When the surface of the top sheet of the comparison product was observed with a microscope, impurities (such as cell fragments and crystals) in the urine were observed. The urine of bedridden elderly contains more impurities, such as cell fragments and crystals, than general adult urine, and it is assumed that the remaining of the impurities in the top sheet causes the reduction in liquid permeability of the top sheet.

In contrast, when the product of the present invention was used, the first, second, and third absorption times for urine sample A were 8 seconds, 17 seconds, and 26 seconds, respectively, whereas the first, second, and third absorption times for urine sample B were 9 seconds, 20 seconds, and 40 seconds, respectively, and the first, second and third absorption times for urine sample C were 10 seconds, 32 seconds, and 59 seconds, respectively. The urine absorption time was notably reduced compared to the comparison product.

REFERENCE SIGNS LIST

100 Urine-absorbing pad
200 Exterior body
111, 211 Abdomen side section
112, 212 Crotch section
113, 213 Back side section
120, 220 Liquid-permeable top sheet
121, 220 Top sheet skin side surface
122 Ridge (example of protrusions)
123 Groove (example of recess)
124 Ridge-groove structure (example of irregular structure)
130, 230 Liquid-impermeable back sheet
140, 240 Absorbent body
140*a* First absorbing layer
140*b* Second absorbing layer
141 Through-hole
141*a* Through-hole of the first absorbing layer
141*b* Through-hole of the second absorbing layer
142, 143 Compressed portion
160 Liquid-absorbing sheet
163 Absorbent polymer layer
250*a*, 250*b* Side sheet
255*a*, 255*b* Leakage preventing section

The invention claimed is:

1. An absorbent article, comprising a liquid-permeable top sheet, a liquid-impermeable back sheet, and a liquid-absorbing absorbent body disposed between the top sheet and the back sheet, and having a lengthwise direction, a widthwise direction, and a thickness direction that are mutually orthogonal;
  wherein the top sheet is a nonwoven fabric with a skin side surface on which protrusions are formed;
  wherein the absorbent body has a through-hole penetrating through the absorbent body in the thickness direction or a recess that opens to a side of the top sheet;
  wherein the absorbent body has a first absorbing layer and a second absorbing layer having a maximum width which is smaller than a minimum width of the first absorbing layer;
  wherein the second absorbing layer is located nearer to the back sheet than the first absorbing layer;
  wherein the absorbent article further comprises a liquid-absorbing sheet having a liquid-permeable first sheet, a liquid-permeable second sheet, and an absorbent polymer layer disposed between the first sheet and the second sheet;
  wherein the liquid-absorbing sheet is disposed between the top sheet and the absorbent body;
  wherein the liquid-absorbing sheet does not overlap the through-hole or recess in the thickness direction; and
  wherein both edges of the absorbent polymer layer are located inside both edges of the first absorbing layer and outside both edges of the second absorbing layer in the widthwise direction of the absorbent article.

2. The absorbent article according to claim 1, wherein the protrusions are ridges extending in the lengthwise direction.

3. The absorbent article according to claim 1, wherein the through-hole or recess extends in the lengthwise direction, through a center in the widthwise direction of the absorbent body.

4. The absorbent article according to claim 1, wherein the absorbent body has a compressed part which integrates the absorbent body in the thickness direction; and wherein the compressed part is formed on an outer side in the widthwise direction from the through-hole or recess.

5. The absorbent article according to claim 1, wherein a content of fibers oriented in the thickness direction at the protrusions of the nonwoven fabric is higher than a content of fibers oriented in the thickness direction at a section other than the protrusions of the nonwoven fabric.

6. The absorbent article according to claim 1, wherein the absorbent article has an abdomen side section, a crotch section and a back side section, aligned in the lengthwise direction;
   wherein the through-hole or recess is located in the crotch section; and
   wherein the liquid-absorbing sheet is located in the back side section.

7. A wearable article, comprising:
   an exterior body comprising a liquid-permeable top sheet with a mounting surface and a liquid-impermeable back sheet, and having an abdomen side section, a crotch section, and a back side section; and
   an absorbent article mounted on the mounting surface in a detachable manner,
   wherein the absorbent article includes
      a liquid-permeable top sheet,
      a liquid-impermeable back sheet,
      a liquid-absorbing absorbent body disposed between the top sheet and the back sheet, and
      a liquid-absorbing sheet having a liquid-permeable first sheet, a liquid-permeable second sheet, and an absorbent polymer layer disposed between the first sheet and the second sheet;
   wherein the absorbent article has a lengthwise direction, a widthwise direction, and a thickness direction that are mutually orthogonal;
   wherein the top sheet of the absorbent article is a nonwoven fabric with a skin side surface on which protrusions are formed;
   wherein the absorbent body has a through-hole penetrating through the absorbent body in the thickness direction or a recess that opens to a side of the top sheet of the absorbent article;
   wherein the absorbent body has a first absorbing layer and a second absorbing layer having a maximum width which is smaller than a minimum width of the first absorbing layer;
   wherein the second absorbing layer is located nearer to the back sheet of the absorbent article than the first absorbing layer;
   wherein the liquid-absorbing sheet is disposed between the top sheet of the absorbent article and the absorbent body;
   wherein the liquid-absorbing sheet does not overlap the through-hole or recess in the thickness direction; and
   wherein both edges of the absorbent polymer layer are located inside both edges of the first absorbing layer and outside both edges of the second absorbing layer in the widthwise direction of the absorbent article.

8. The wearable article according to claim 7, wherein the exterior body comprises:
   a first leakage preventing section capable of rising up from the mounting surface and having an anchored edge which is anchored to the mounting surface and a free edge capable of being separated from the mounting surface;
   a first elastic member attached to the free edge of the first leakage preventing section in a stretched state, both sides of the first elastic member in a stretching direction are anchored to the mounting surface;
   a second leakage preventing section capable of rising up from the mounting surface and having an anchored edge which is anchored to the mounting surface and a free edge capable of being separated from the mounting surface; and
   a second elastic member attached to the free edge of the second leakage preventing section in a stretched state, both sides of the second elastic member in the stretching direction are anchored to the mounting surface;
   wherein the absorbent article is disposed on the mounting surface and both edge sections of the absorbent article in the widthwise direction are respectively located between the mounting surface and the first leakage preventing section and between the mounting surface and the second leakage preventing section; and
   wherein the absorbent polymer layer has, in the widthwise direction, a maximum width which is larger than the distance, in the widthwise direction, between the first elastic member and the second elastic member.

9. The absorbent article according to claim 2, wherein the through-hole or recess extends in the lengthwise direction, through a center in the widthwise direction of the absorbent body.

10. The absorbent article according to claim 2, wherein the absorbent body has a compressed part which integrates the absorbent body in the thickness direction; and wherein the compressed part is formed on an outer side in the widthwise direction from the through-hole or recess.

11. The absorbent article according to claim 3, wherein the absorbent body has a compressed part which integrates the absorbent body in the thickness direction; and wherein the compressed part is formed on an outer side in the widthwise direction from the through-hole or recess.

12. The absorbent article according to claim 2, wherein a content of fibers oriented in the thickness direction at the protrusions of the nonwoven fabric is higher than a content of fibers oriented in the thickness direction at a section other than the protrusions of the nonwoven fabric.

13. The absorbent article according to claim 3, wherein a content of fibers oriented in the thickness direction at the protrusions of the nonwoven fabric is higher than a content of fibers oriented in the thickness direction at a section other than the protrusions of the nonwoven fabric.

14. The absorbent article according to claim 4, wherein a content of fibers oriented in the thickness direction at the protrusions of the nonwoven fabric is higher than a content of fibers oriented in the thickness direction at a section other than the protrusions of the nonwoven fabric.

* * * * *